(12) United States Patent
Claypool et al.

(10) Patent No.: US 8,114,086 B2
(45) Date of Patent: Feb. 14, 2012

(54) NAVIGATED CUT GUIDE LOCATOR

(75) Inventors: Jody L. Claypool, Columbia City, IN (US); Shawn E. McGinley, Fort Wayne, IN (US); Sudip Hui, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1524 days.

(21) Appl. No.: 11/344,273

(22) Filed: Jan. 31, 2006

(65) Prior Publication Data

US 2006/0122618 A1    Jun. 8, 2006

Related U.S. Application Data

(63) Continuation-in-part of application No. 10/979,734, filed on Nov. 2, 2004, now Pat. No. 7,993,341, which is a continuation-in-part of application No. 10/795,830, filed on Mar. 8, 2004, now abandoned.

(51) Int. Cl.
*A61B 17/15*    (2006.01)
(52) U.S. Cl. .......................................... 606/87; 606/130
(58) Field of Classification Search .................... 606/88, 606/96, 130, 86 R, 87, 97
See application file for complete search history.

(56) References Cited

U.S. PATENT DOCUMENTS

| | | | |
|---|---|---|---|
| 4,211,228 A | 7/1980 | Cloutier | |
| 4,421,112 A | 12/1983 | Mains et al. | |
| 4,457,307 A | 7/1984 | Stillwell | |
| 4,467,801 A | 8/1984 | Whiteside | |
| 4,487,203 A | 12/1984 | Androphy | |
| 4,493,317 A | 1/1985 | Klaue | 606/69 |
| 4,501,266 A | 2/1985 | McDaniel | |
| 4,524,766 A | 6/1985 | Petersen | 606/88 |
| 4,566,448 A | 1/1986 | Rohr, Jr. | |
| 4,567,886 A | 2/1986 | Petersen | |
| 4,653,488 A | 3/1987 | Kenna | |
| 4,736,737 A | 4/1988 | Fargie et al. | |
| 4,759,350 A * | 7/1988 | Dunn et al. | 606/82 |
| 4,841,975 A | 6/1989 | Woolson | 600/425 |
| 4,892,093 A | 1/1990 | Zarnowski et al. | |
| 4,907,577 A | 3/1990 | Wu | 606/87 |
| 4,913,137 A | 4/1990 | Azer et al. | |
| 4,952,213 A | 8/1990 | Bowman et al. | |
| 5,002,545 A | 3/1991 | Whiteside et al. | |
| 5,002,547 A | 3/1991 | Poggie et al. | 606/88 |
| 5,007,936 A | 4/1991 | Woolson | 128/898 |
| 5,037,423 A | 8/1991 | Kenna | |
| 5,053,037 A | 10/1991 | Lackey | |
| 5,092,037 A | 3/1992 | Pinkerton | |
| 5,100,408 A | 3/1992 | Lackey | |
| 5,116,338 A | 5/1992 | Poggie et al. | 606/90 |
| 5,154,717 A | 10/1992 | Matsen, III et al. | 606/53 |
| 5,171,277 A | 12/1992 | Roger | 606/86 |
| 5,230,338 A | 7/1993 | Allen et al. | 600/429 |

(Continued)

FOREIGN PATENT DOCUMENTS

DE    10207035A1 A1    9/2003

(Continued)

OTHER PUBLICATIONS

The Response filed Sep. 27, 2006 to the European Office Action mailed Apr. 7, 2006, in related European Patent Application No. 05251367.8.

(Continued)

*Primary Examiner* — Thomas C. Barrett
*Assistant Examiner* — Christian Sevilla
(74) *Attorney, Agent, or Firm* — Faegre Baker Daniels

(57) ABSTRACT

A navigated guide is provided for establishing datums used to position subsequent components during a surgical procedure.

18 Claims, 15 Drawing Sheets

U.S. PATENT DOCUMENTS

| | | | |
|---|---|---|---|
| 5,234,433 A | 8/1993 | Bert et al. | |
| 5,251,127 A | 10/1993 | Raab | 606/130 |
| 5,275,603 A | 1/1994 | Ferrante et al. | |
| 5,282,803 A | 2/1994 | Lackey | |
| 5,305,203 A | 4/1994 | Raab | 606/1 |
| 5,342,367 A | 8/1994 | Ferrante et al. | |
| 5,342,368 A | 8/1994 | Petersen | |
| 5,364,401 A | 11/1994 | Ferrante et al. | |
| 5,364,402 A | 11/1994 | Mumme et al. | |
| 5,411,505 A | 5/1995 | Mumme | |
| 5,413,579 A | 5/1995 | Tom Du Toit | 606/87 |
| 5,417,694 A | 5/1995 | Marik et al. | |
| 5,431,653 A | 7/1995 | Callaway | |
| 5,431,656 A | 7/1995 | Clift, Jr. et al. | |
| 5,445,642 A | 8/1995 | McNulty et al. | |
| 5,454,816 A | 10/1995 | Ashby | |
| 5,470,335 A | 11/1995 | Du Toit | 606/73 |
| 5,474,559 A | 12/1995 | Bertin et al. | 606/89 |
| 5,484,446 A | 1/1996 | Burke et al. | 606/87 |
| 5,486,178 A | 1/1996 | Hodge | |
| 5,486,180 A | 1/1996 | Dietz et al. | 606/87 |
| 5,514,139 A | 5/1996 | Goldstein et al. | |
| 5,514,140 A | 5/1996 | Lackey | |
| 5,551,429 A | 9/1996 | Fitzpatrick et al. | 600/426 |
| 5,562,674 A | 10/1996 | Stalcup et al. | 606/88 |
| 5,569,261 A | 10/1996 | Marik et al. | |
| 5,584,838 A | 12/1996 | Rona et al. | 606/96 |
| 5,593,411 A | 1/1997 | Stalcup et al. | 606/88 |
| 5,597,379 A | 1/1997 | Haines et al. | |
| 5,601,570 A | 2/1997 | Altmann et al. | |
| 5,611,802 A | 3/1997 | Samuelson et al. | |
| 5,628,750 A | 5/1997 | Whitlock et al. | |
| 5,634,929 A | 6/1997 | Misko et al. | 606/130 |
| 5,643,272 A | 7/1997 | Haines et al. | |
| 5,649,928 A | 7/1997 | Grundei | |
| 5,669,914 A | 9/1997 | Eckhoff | |
| 5,676,668 A | 10/1997 | McCue et al. | |
| 5,681,316 A | 10/1997 | DeOrio et al. | |
| 5,682,886 A | 11/1997 | Delp et al. | 600/407 |
| 5,683,397 A | 11/1997 | Vendrely et al. | |
| 5,683,398 A | 11/1997 | Carls et al. | |
| 5,720,752 A | 2/1998 | Elliott et al. | |
| 5,743,915 A | 4/1998 | Bertin et al. | 606/88 |
| 5,743,916 A | 4/1998 | Greenberg et al. | 606/102 |
| 5,748,767 A | 5/1998 | Raab | 382/128 |
| 5,788,700 A | 8/1998 | Morawa et al. | |
| 5,810,831 A | 9/1998 | D'Antonio | |
| 5,834,759 A | 11/1998 | Glossop | 250/203.1 |
| 5,871,018 A | 2/1999 | Delp et al. | 128/898 |
| 5,888,034 A | 3/1999 | Greenberg | 408/115 R |
| 5,891,158 A | 4/1999 | Manwaring et al. | 606/130 |
| 5,904,691 A | 5/1999 | Barnett et al. | 606/130 |
| 5,911,723 A | 6/1999 | Ashby et al. | |
| 5,921,992 A | 7/1999 | Costales | 606/130 |
| 5,995,738 A | 11/1999 | DiGioia, III et al. | 703/11 |
| 6,002,859 A | 12/1999 | DiGioia, III et al. | 703/11 |
| 6,022,377 A | 2/2000 | Nuelle et al. | |
| 6,033,415 A | 3/2000 | Mittelstadt et al. | 606/130 |
| 6,056,756 A | 5/2000 | Eng et al. | |
| 6,074,394 A | 6/2000 | Krause | 606/86 |
| 6,077,270 A | 6/2000 | Katz | |
| 6,081,741 A | 6/2000 | Hollis | 600/424 |
| 6,090,114 A | 7/2000 | Matsuno et al. | |
| 6,096,043 A | 8/2000 | Techiera et al. | |
| 6,096,082 A | 8/2000 | Stegmuller et al. | |
| 6,103,081 A | 8/2000 | Morris et al. | |
| 6,106,529 A | 8/2000 | Techiera | |
| 6,162,228 A | 12/2000 | Durham | 606/96 |
| 6,167,145 A | 12/2000 | Foley et al. | 382/128 |
| 6,234,429 B1 | 5/2001 | Yang | |
| 6,258,103 B1 | 7/2001 | Saracione | |
| 6,261,300 B1 | 7/2001 | Carol et al. | |
| 6,267,762 B1 | 7/2001 | Millard et al. | |
| 6,267,770 B1 | 7/2001 | Truwit | 606/130 |
| 6,285,902 B1 | 9/2001 | Kienzle, III et al. | 600/427 |
| 6,306,146 B1 | 10/2001 | Dinkler | |
| 6,338,716 B1 | 1/2002 | Hossack | 600/459 |
| 6,342,056 B1 | 1/2002 | Mac-Thiong | 606/96 |
| 6,396,939 B1 | 5/2002 | Hu et al. | 382/128 |
| 6,402,762 B2 | 6/2002 | Hunter | 606/130 |
| 6,430,434 B1 | 8/2002 | Mittelstadt | 600/426 |
| 6,450,978 B1 | 9/2002 | Brosseau | 600/595 |
| 6,458,135 B1 | 10/2002 | Harwin et al. | |
| 6,477,400 B1 | 11/2002 | Barrick | 600/426 |
| 6,490,467 B1 | 12/2002 | Bucholz | 600/407 |
| 6,490,475 B1 | 12/2002 | Seeley | 600/426 |
| 6,503,249 B1 | 1/2003 | Krause | 606/62 |
| 6,533,790 B1 | 3/2003 | Liu | 606/73 |
| 6,551,325 B2 | 4/2003 | Neubauer et al. | |
| 6,554,837 B1 | 4/2003 | Hauri et al. | |
| 6,575,980 B1 | 6/2003 | Robie et al. | |
| 6,595,997 B2 | 7/2003 | Axelson, Jr. et al. | |
| 6,638,281 B2 | 10/2003 | Gorek | 606/96 |
| 6,648,896 B2 | 11/2003 | Overes et al. | |
| 6,685,711 B2 | 2/2004 | Axelson, Jr. et al. | |
| 6,695,848 B2 | 2/2004 | Haines | |
| 6,712,824 B2 | 3/2004 | Millard et al. | |
| 6,740,092 B2 | 5/2004 | Lombardo et al. | |
| 6,758,850 B2 | 7/2004 | Smith et al. | |
| 6,796,986 B2 | 9/2004 | Duffner | |
| 6,859,661 B2 | 2/2005 | Tuke | |
| 6,920,347 B2 | 7/2005 | Simon et al. | |
| 6,925,339 B2 | 8/2005 | Grimm et al. | |
| 6,932,823 B2 | 8/2005 | Grimm et al. | |
| 6,942,700 B2 | 9/2005 | Williamson | |
| 6,962,593 B2 | 11/2005 | Sanford et al. | |
| 6,989,015 B2 | 1/2006 | Daum et al. | |
| 7,104,996 B2 | 9/2006 | Bonutti | |
| 2002/0068942 A1* | 6/2002 | Neubauer et al. | 606/88 |
| 2002/0133160 A1 | 9/2002 | Axelson, Jr. et al. | |
| 2002/0133162 A1 | 9/2002 | Axelson, Jr. et al. | |
| 2002/0151894 A1 | 10/2002 | Melkent | 606/61 |
| 2002/0165552 A1 | 11/2002 | Duffner | |
| 2002/0198531 A1 | 12/2002 | Millard et al. | |
| 2003/0069585 A1 | 4/2003 | Axelson, Jr. et al. | |
| 2003/0069591 A1 | 4/2003 | Carson et al. | |
| 2003/0083667 A1 | 5/2003 | Ralph | 606/96 |
| 2003/0171757 A1 | 9/2003 | Coon et al. | |
| 2003/0181919 A1 | 9/2003 | Gorek | 606/96 |
| 2003/0187351 A1 | 10/2003 | Franck | |
| 2003/0212403 A1 | 11/2003 | Swanson | |
| 2003/0220689 A1 | 11/2003 | Ritland et al. | |
| 2003/0225329 A1 | 12/2003 | Rossner et al. | |
| 2004/0039396 A1 | 2/2004 | Couture et al. | |
| 2004/0073228 A1 | 4/2004 | Kienzle | 606/96 |
| 2004/0122305 A1 | 6/2004 | Grimm | 600/407 |
| 2004/0153066 A1 | 8/2004 | Coon et al. | |
| 2004/0153083 A1 | 8/2004 | Nemec et al. | |
| 2004/0171930 A1 | 9/2004 | Grimm et al. | |
| 2004/0172044 A1 | 9/2004 | Grimm | 606/130 |
| 2005/0021039 A1 | 1/2005 | Cusick et al. | |
| 2005/0049603 A1 | 3/2005 | Calton et al. | |
| 2005/0055028 A1 | 3/2005 | Haines | |
| 2005/0070910 A1 | 3/2005 | Keene | |
| 2005/0149039 A1 | 7/2005 | Haines et al. | |
| 2005/0149040 A1 | 7/2005 | Haines | |
| 2005/0149041 A1 | 7/2005 | McGinley et al. | |
| 2005/0171545 A1 | 8/2005 | Walsh et al. | |
| 2005/0182415 A1 | 8/2005 | Steffensmeier et al. | |
| 2005/0187557 A1 | 8/2005 | Collazo | |
| 2005/0203528 A1 | 9/2005 | Couture et al. | |
| 2005/0209598 A1 | 9/2005 | Grimm | |
| 2005/0209605 A1 | 9/2005 | Grimm et al. | |
| 2005/0215888 A1 | 9/2005 | Grimm et al. | |
| 2005/0234454 A1 | 10/2005 | Chin | |
| 2005/0234465 A1 | 10/2005 | McCombs | |
| 2005/0234466 A1 | 10/2005 | Stallings | |
| 2005/0261699 A1 | 11/2005 | Neubauer et al. | |
| 2005/0273113 A1 | 12/2005 | Kuczynski | |
| 2005/0273114 A1 | 12/2005 | Novak | |
| 2006/0190010 A1 | 8/2006 | Easton | |
| 2007/0149977 A1 | 6/2007 | Heavener et al. | |

FOREIGN PATENT DOCUMENTS

| | | |
|---|---|---|
| EP | 0538152 | 8/1995 |
| EP | 0384562 | 7/1996 |
| EP | 0556998 | 6/1997 |
| EP | 0839501 | 7/1998 |
| EP | 0720834 | 6/1999 |

| | | |
|---|---|---|
| EP | 1302167A2 A2 | 4/2003 |
| EP | 1323386 | 7/2003 |
| EP | 1424042 | 2/2004 |
| EP | 1430842 | 6/2004 |
| EP | 1442712 | 8/2004 |
| EP | 1444962A2 A2 | 8/2004 |
| EP | 0778751 | 5/2005 |
| EP | 1574177 | 9/2005 |
| EP | 1579812 | 9/2005 |
| JP | 11244315 | 9/1999 |
| WO | WO 96/07361 | 3/1996 |
| WO | WO 9629940 | 10/1996 |
| WO | WO97/29710 A1 | 8/1997 |

OTHER PUBLICATIONS

Nexgen Complete Knee Solution, The Zimmer Institute Surgical Technique MIS Quad-Sparing Surgical Technique for Total Knee Arthroplasty, 2004.

U.S. Appl. No. 10/795,830, filed Mar. 8, 2004, Grimm.

U.S. Appl. No. 10/795,621, filed Mar. 8, 2004, Grimm.

U.S. Appl. No. 10/979,734, filed Nov. 2, 2004, Grimm.

U.S. Appl. No. 11/287,839, filed Nov. 28, 2005, Heavener.

Nexgen Complete Knee Solution, Intramedullary Instrumentation Surgical Technique, for the NexGen Cruciate Retaining & Legacy Posterior Stabilized Knee, Zimmer, Inc. 97-5973-102 Rev. 1 (1998).

Nexgen Complete Knee Solution, Posterior Reference, Multi-Referenced 4-in-1 Femoral Instrumentation; Posterior Reference Surgical Technique, for NexGen Cruciate Retaining & Legacy Posterior Stabilized Knees, Zimmer, Inc. 97-5973-402 Rev1 (1998).

Nexgen Complete Knee Solution, Micro-Mill Instrumentation Surgical Technique, for The NexGen Cruciate Retaining & Legacy Posterior Stabilized Knee, Zimmer, Inc. 97-5970-103 (1998).

Nexgen Complete Knee Solution, Revision Instrumentation Surgical Technique for Legacy Knee Constrained Condylar Knee, Zimmer, Inc. 97-5994-202 (2001).

Revision Knee Arthroplasty Surgical Guidelines, $2^{nd}$ Edition, by Kelly Vince, M.D., John Insall, M.D., Robert Booth, Jr., M.D. and Giles Scuderi, M.D., Zimmer, Inc. 97-5224-03 Rev. 1 (1999).

* cited by examiner

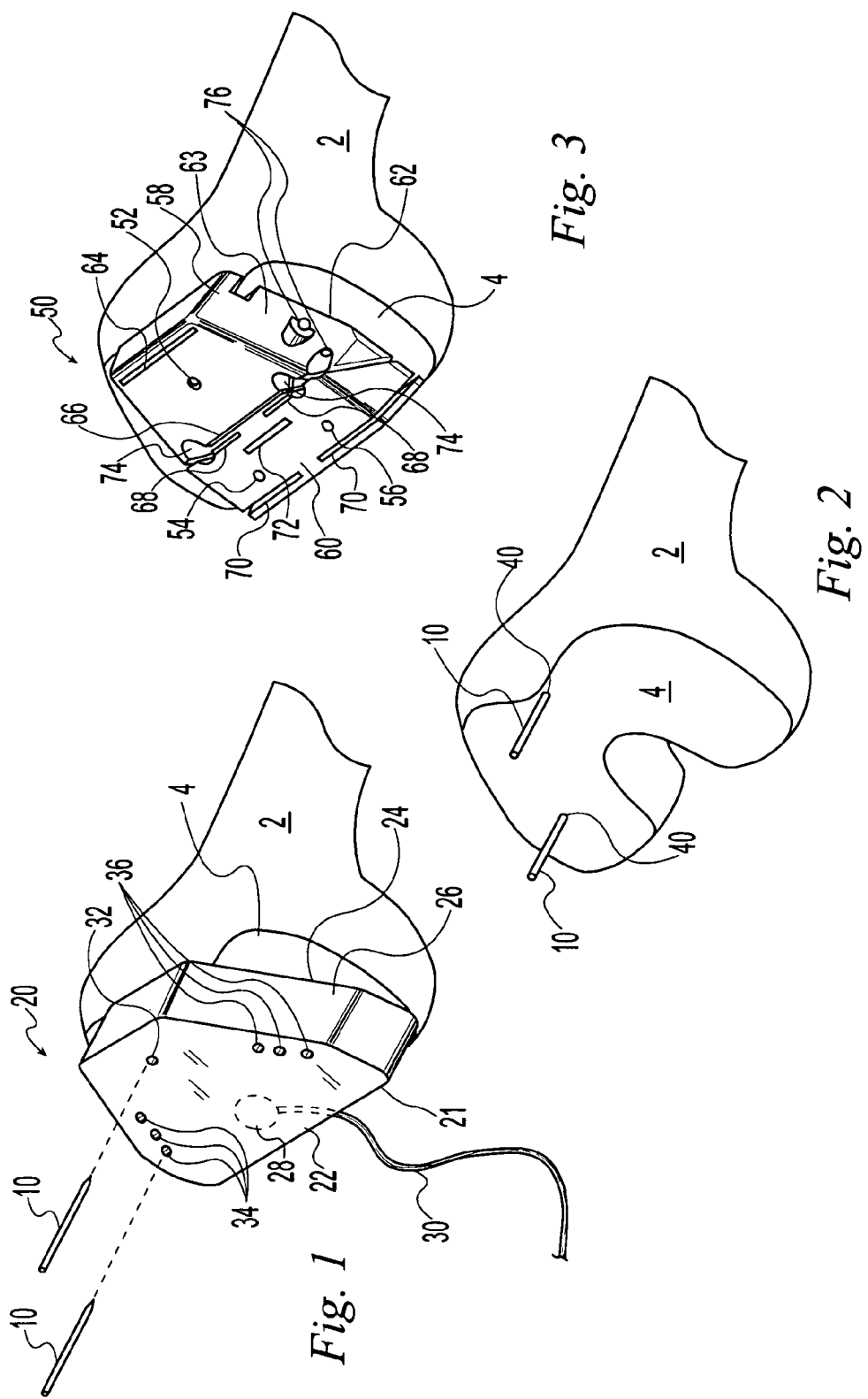

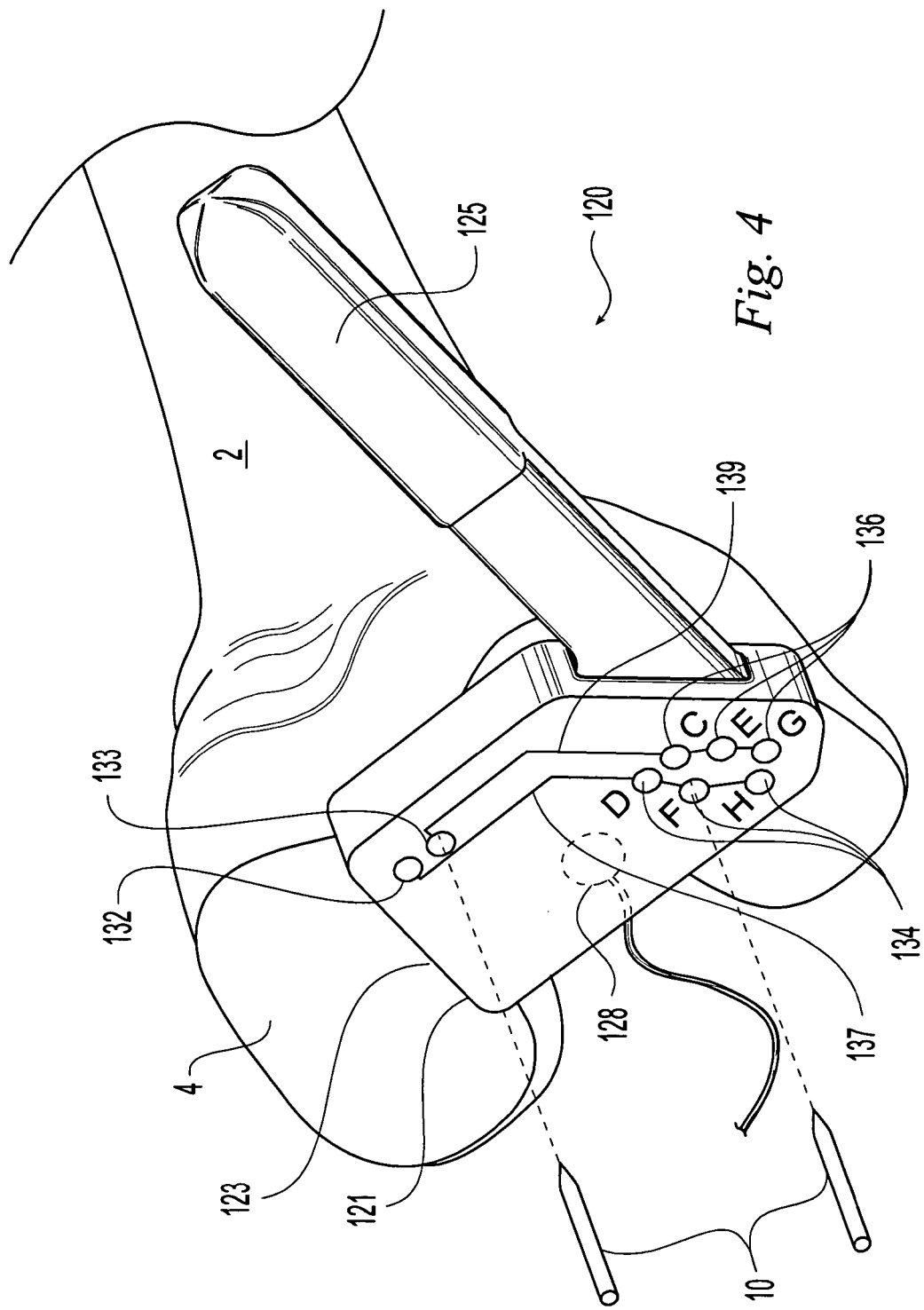

NAVIGATED CUT GUIDE LOCATOR

CROSS-REFERENCE TO RELATED APPLICATIONS

This application is a continuation-in-part of U.S. application Ser. No. 10/979,734, filed Nov. 2, 2004, now U.S. Pat. No. 7,993,341 which is a continuation-in-part of U.S. application Ser. No. 10/795,830, filed Mar. 8, 2004 now abandoned.

BACKGROUND

The present invention relates to surgical components used in conjunction with a surgical navigation system. In particular, the present invention relates to a navigated instrument for guiding subsequent components during a surgical procedure.

Many surgical procedures are now performed with surgical navigation systems in which sensors detect tracking elements attached in known relationship to an object in the surgical suite such as a surgical instrument, implant, or patient body part. The sensor information is fed to a computer that then triangulates the three dimensional position of the tracking elements within the surgical navigation system coordinate system. Thus, the computer can resolve the position and orientation of the object and display the position and orientation for surgeon guidance. For example, the position and orientation can be shown superimposed on an image of the patient's anatomy obtained via X-ray, CT scan, ultrasound, or other imaging technology.

However, most surgical procedures are performed using conventional instruments in which the various components of the surgery are aligned mechanically by the surgeon by visualizing and/or palpating anatomic landmarks. During these procedures, surgical components in the form of instruments to prepare a bone, provisional components to verify sizing, implant components and/or other suitable components are placed in a surgical site. These components often have position and orientation requirements for them to operate properly. For example, a bone cutting guide must be aligned on the bone in the proper orientation to guide a cutter to produce a cut surface in a desire location.

SUMMARY

The present invention provides a navigated cut guide locator and method for guiding subsequent surgical components.

In one aspect of the invention, a navigated guide is provided for use with a surgical navigation system to establish a datum relative to a surgical site to guide placement of a surgical cut guide. The cut guide has a cut slot with a slot thickness, a slot width, and a slot depth. The slot defines a cut plane and is engageable with a cutter to guide the cutter within the cut plane. The navigated guide includes a plate shaped body representative of the cut plane. The body is slidingly engageable with the cut slot. The navigated guide further includes a way for being tracked by the surgical navigation system to position the body at a desired position relative to the surgical site.

In another aspect of the invention, a surgical system is provided for use at an orthopaedic surgical site to guide a cutter to cut a bone. The system includes a surgical navigation system, a cut guide, and a navigated guide. The surgical navigation system includes a way for tracking the position of an object during a surgical procedure. The cut guide includes a cut slot for guiding the cutter in a cut plane to form a planar surface on the distal end of the femur. The navigated guide includes a plate shaped body representative of the cut plane. The body is slidingly engageable with the cut slot. The navigated guide further has a way for being tracked by the surgical navigation system to position the navigated guide at a desired position relative to the surgical site.

In another aspect of the invention, a method of guiding a cutter at an orthopaedic surgical site to cut a bone includes activating a surgical navigation system to track the position of a navigated guide, the navigated guide comprising a plate shaped body representative of a cut plane; anchoring the navigated guide relative to the surgical site in a desired position as indicated by the surgical navigation system; and engaging a cut guide with the navigated guide by sliding a slot in the cut guide over the plate shaped body of the navigated guide to align the cut slot with the cut plane.

BRIEF DESCRIPTION OF THE DRAWINGS

Various illustrative examples of the present invention will be discussed with reference to the appended drawings. These drawings depict only illustrative examples of the invention and are not to be considered limiting of its scope.

FIG. 1 is a perspective view of an illustrative navigated guide according to the present invention in use to establish a datum relative to a bone;

FIG. 2 is a perspective view of the bone of FIG. 1 showing the datum established with the navigated guide of FIG. 1;

FIG. 3 is a perspective view showing a surgical component positioned using the datum of FIG. 2;

FIG. 4 is a perspective view of an illustrative alternative arrangement for the navigated guide of FIG. 1;

DESCRIPTION OF THE ILLUSTRATED EMBODIMENTS

Figure 5:
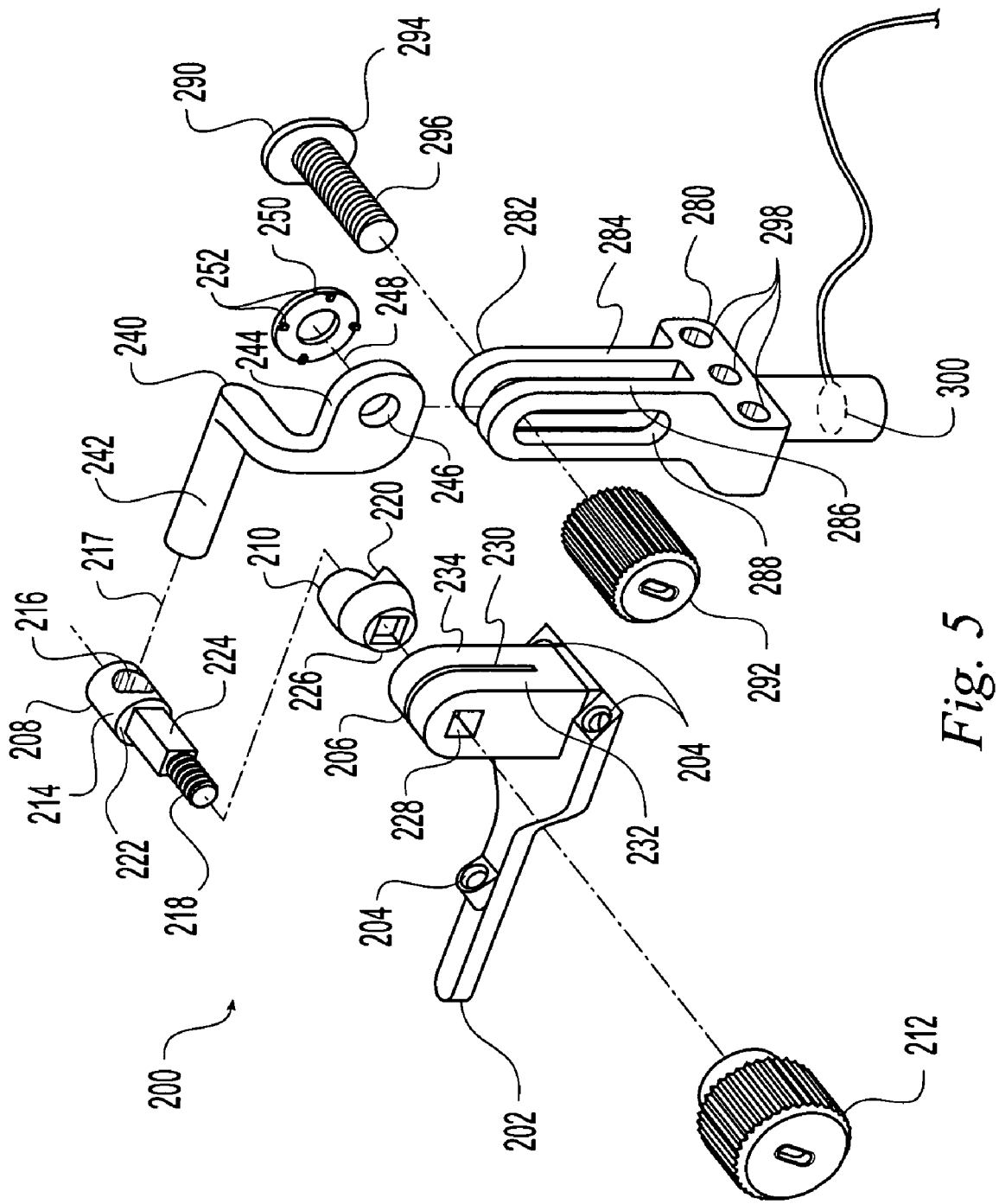
FIG. 5 is an exploded perspective view of an illustrative alternative arrangement for the navigated guide of FIG. 1 having an adjustment mechanism.

Embodiments of a navigated guide may be configured to guide a variety of surgical components. For example, a navigated orthopaedic guide may be used to establish a datum relative to a bone such as one or more pins, screws, bars, fins, rails, dovetails, planar surfaces, holes, slots, notches, and/or any other suitable datum in or on a bone. The datum may be used to reference the position and/or orientation of a subsequent surgical component including cutting instruments, reaming instruments, templates, drill guides, provisional implants, implants, and/or other components for any suitable surgical site. Examples of surgical sites include hip joints, knee joints, vertebral joints, shoulder joints, elbow joints, ankle joints, digital joints of the hand and feet, the jaw, the skull, fracture sites, tumor sites, and/or other suitable surgical sites. The navigated guide of the present invention may be used to establish datums that may be referenced by components that are not otherwise usable with a surgical navigation system. Thus, the navigated guide may be used to provide the benefits of three dimensional surgical navigation technology while using existing non-navigated components. The navigated guide may be configured to establish a separate intermediate datum or it may serve as the datum itself to engage and guide a subsequent surgical component directly. A guide that serves directly as the datum may include one or more pins, screws, bars, fins, rails, dovetails, planar surfaces, holes, slots, notches, and/or other feature that directly engages the subsequent component to guide it relative to a surgical site.

FIGS. 1-3 depict an illustrative navigated orthopaedic guide 20 configured to guide the placement of datum pins 10 on which a femoral cut guide 50 is positioned to guide the cutting of a femur 2 to receive a femoral component in knee replacement surgery. The guide 20 includes a body 21 having a front surface 22, a back surface 24 opposite the front surface 22, and a circumferential side wall 26 extending from the front surface 22 to the back surface 24. In the illustrative example, the orthopaedic guide 20 includes a tracking element in the form of an electromagnetic coil 28 embedded in the body 21 between the front and back surfaces 22, 24 and within the perimeter of the side wall 26. The coil 28 includes a lead 30 extending from the coil 28 and out of the body 21 to connect to the surgical navigation system for transmitting electrical signals between the surgical navigation system and the coil 28. When the coil 28 is placed within an electromagnetic field, it generates an electrical charge that is transmitted to the surgical navigation system such that the three dimensional position and orientation of the coil 28, and thus the orthopaedic guide 20, can be related to a surgical navigation coordinate system. For example, the surgical navigation system may include multiple sensors at known locations that receive signals from the coil 28 and feed the information to a computer. The computer may then triangulate the three dimensional position of the coil within the surgical navigation coordinate system. The surgical navigation system may then determine the position and orientation of the orthopaedic guide 20 by detecting the position and orientation of the coil 28 and resolving the position and orientation of the orthopaedic guide 20 from the known relationship between the coil 28 and the orthopaedic guide 20.

While the illustrative example depicts an active electromagnetic tracking element, the tracking element may be detectable electromagnetically, acoustically, by imaging, or by other suitable detection means. Furthermore, the tracking element may be active or passive. Examples of active tracking elements may include electromagnetic field emitters in an electromagnetic system (such as the illustrative coil 28), light emitting diodes in an imaging system, and ultrasonic emitters in an acoustic system, among others. Examples of passive tracking elements may include elements with reflective surfaces. For example, reflective spheres or discs may be attached to the orthopaedic guide and detected by an imaging system.

The orthopaedic guide 20 includes means for establishing a datum on or in a bone to guide subsequent components. In the illustrative guide 20, holes 32, 34, 36 extend through the orthopaedic guide 20 from the front surface 22 to the back surface 24. The holes may guide the placement of pins 10, screws, or other datums. For example, a drill bit may be guided along one or more of the holes 32, 34, 36 to create a hole 40 (FIG. 2) in the underlying bone 2. A pin 10 may then be inserted into the hole in the bone 2. Alternatively, a self-drilling pin may be used. Alternatively, the pin 10 may be omitted and the hole 40 formed in the bone 2 may itself serve as a datum. Alternatively, the orthopaedic guide 20 may include a notch, slot, guide surface, or other feature to guide forming a notch, slot, or other datum in the bone 2. Alternatively, the orthopaedic guide 20 may include a slot, notch, guide surface, or other feature to guide placing a bar, rail, or other datum in or on the bone 2.

Once the datum has been positioned on the bone 2, a surgical component may be referenced to the datum to correctly position the surgical component. For example, in FIG. 3, a femoral cut guide 50 includes holes 52, 54, and 56 for receiving datum pins 10 set using the orthopaedic guide 20. Alternatively, the surgical component may include protrusions for engaging holes 40 formed using the orthopaedic guide 20, or other features for engaging other types of datums positioned using the orthopaedic guide 20. The femoral cut guide 50 includes a body 58 having a front surface 60, a back surface 62, and a circumferential side wall 63 extending from the front surface 60 to the back surface 62. The datum receiving holes 52, 54, 56 extend from the front surface 60 to the back surface 62. A plurality of slots 64, 66, 68, 70, 72 are formed through the cut guide 50 from the front surface 60 to the back surface 62 to guide a cutter to shape the end of the femur 2 to receive a femoral knee implant. For example, a posterior cut slot 70 may guide a saw blade to cut a posterior facet on the femur 2. A posterior chamfer cut slot 68 may guide a saw blade to cut a posterior chamfer facet on the femur 2. An anterior cut slot 64 may guide a saw blade to cut an anterior facet on the femur 2. An anterior chamfer cut slot 66 may guide a saw blade to cut an anterior chamfer facet on the femur 2. A trochlear recess cut slot 72 may guide a saw blade to cut the base of a trochlear recess on the femur 2. In addition, drill guide holes 74 may guide a drill bit to form post holes in the femur for receiving a fixation post of a femoral implant. Fixation holes 76 are positioned to receive additional pins, screws, or other fasteners to hold the cut guide 50 in place on the bone 2 while the saw cuts and drill holes are made.

In the illustrative guide 20 of FIG. 1, the holes 32, 34, 36 correspond to holes formed in cut guides 50 provided in a range of sizes. The central hole 32 in the orthopaedic guide 20 corresponds to the central hole 52 in the cut guide 50 and is common to all of the sizes of cut guides 50. The additional holes 54, 56 for receiving the datum pins 10 may vary in location by size of the cut guide 50. Therefore, the orthopaedic guide 20 includes multiple locations for the corresponding additional orthopaedic guide holes 34, 36. The additional orthopaedic guide holes 34, 36 may be labeled to identify the size of the cut guide 50 that is planned to be used. The datum pin 10 is then positioned using the correspondingly labeled orthopaedic guide hole 34, 36. Two pins 10 are sufficient to positively locate the cut guide 50.

The use of the orthopaedic guide 20 will now be described in conjunction with the exemplary femoral cut guide 50 surgical component in a procedure to replace the distal end of the femur 2 during knee joint replacement surgery. The surgeon may preoperatively determine the desired intraoperative size and location of the femoral implant. For example, X-ray images, CT data, MRI data, or other patient data may be digitized to form a computer model of the patient's anatomy and superimposed with a model of the available knee implants on a computer screen. The surgeon may then pick the appropriate size of implant and virtually maneuver it to a desired location in the computer model. This positioning information may then be used by the surgical navigation system to guide the surgeon to position the central common hole 32 in the orthopaedic guide 20 at the appropriate position to correctly position the chosen cut guide 50. For example, the surgeon may form the distal cut surface 4 in a conventional manner as is known in the art. The navigated orthopaedic guide 20 may then be positioned on the distal cut surface 4 and maneuvered about until the surgical navigation system indicates that the central hole 32 is in the required position. A datum pin 10 may then be inserted by drilling through the hole 32 into the femur 2 and pressing the datum pin 10 into the drilled hole 40. The orthopaedic guide 20 is thus fixed in a particular anterior-posterior (A/P) and medial-lateral (M/L) position and may now be rotated about the pin 10 in the central hole 32 until the surgical navigation system indicates that another hole 34, 36, corresponding to the planned implant size, is at the correct rotational position. A datum pin 10 may then be inserted by drilling through the appropriate hole 34, 36 into the femur 2 and pressing the datum pin 10 into the drilled hole 40. The orthopaedic guide 20 may now be removed by lifting it off of the datum pins 10. The appropriate femoral cut guide 50 may be positioned on the distal cut surface 4 of the femur 2 by sliding the cut guide 50 over the datum pins 10. The cut guide may be secured to the bone by inserting pins, screws, or other fasteners through one or more of the fixation holes 76 and into the femur 2. Saw blades and drills may be guided using the slots 64, 66, 68, 70, 72 and holes 74 in the cut guide 50 to prepare the femur 2 to receive a particular size of implant in a desired A/P, M/L, and rotational position.

Alternatively, the orthopaedic guide 20 may itself serve as a datum for guiding subsequent components. For example, the orthopaedic guide 20 may include a hole, slot, planar surface, and/or other feature for directly engaging and guiding a subsequent component relative to the surgical coordinate system. For example, the guide slots 64, 66, 68, 70, 72 and holes 74 of the cut guide 50 may be formed directly in the navigated guide 20. However, a navigated guide 20 with all of the features of the cut guide 50 may be more expensive and/or more delicate than the cut guide 50. Since the cut guides 50 are typically provided in a variety of sizes, it may be less costly and/or require less maintenance to provide a single separate navigated guide 20 for establishing a datum as described above. Furthermore, a separate navigated guide may be used to provide the benefits of surgical navigation technology while using existing non-navigated cut guides 50. This significantly reduces the cost of transition from a non-navigated to a navigated procedure by reducing the number of new instruments required.

FIG. 4 illustrates an alternative arrangement for the navigated orthopaedic guide of FIG. 1. The orthopaedic guide 120 of FIG. 4 is approximately one-half the width of the orthopaedic guide 20 of FIG. 1. This smaller orthopaedic guide 120 is well suited for use in minimally invasive surgical procedures in which a reduced size incision is made. The guide 120 includes a body 121 and a tracking element in the form of an electromagnetic coil 128 to permit the surgical navigation system to track the position and orientation of the guide 120. A handle 125 extends from the guide 120 to facilitate insertion of guide into an incision. In a minimally invasive surgical procedure, it may be necessary to slip an edge 123 of the guide 120 under the margins of the incision such that the guide body 121 is largely covered by soft tissue. The handle 125 provides a gripping surface projecting from the incision. The guide body 121 includes a central hole 132 and first and second sets of additional datum guide holes 134, 136. The additional datum guide holes 134, 136 are labeled to indicate the corresponding cut guide 50 associated with each hole. In order to better accommodate the datum guide holes 134, 136 on a half size instrument, an alternate offset central hole 133 is provided. The alternate central hole 133 is associated with the second set of datum guide holes 136 so that the second set of datum guide holes 136 may be offset from and not overlap the first set of datum guide holes 134. A visual cue, such as etched lines 137, 139 may be provided to associate the corresponding central holes 132, 133 and additional datum guide holes 134, 136.

Figure 6:
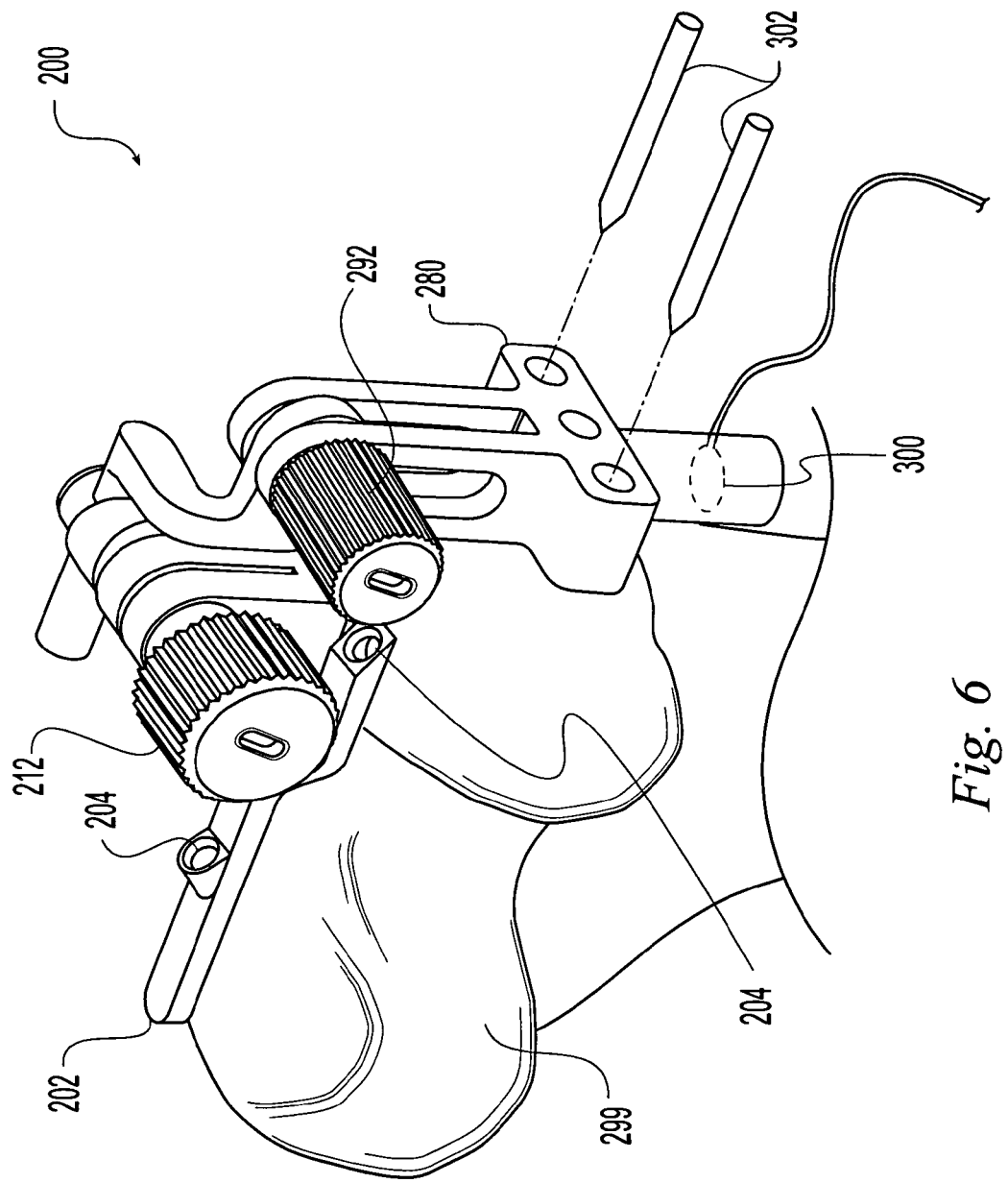
FIG. 6 is a perspective view of the navigated guide of FIG. 5 in use to establish a datum relative to a bone.
Figure 7:
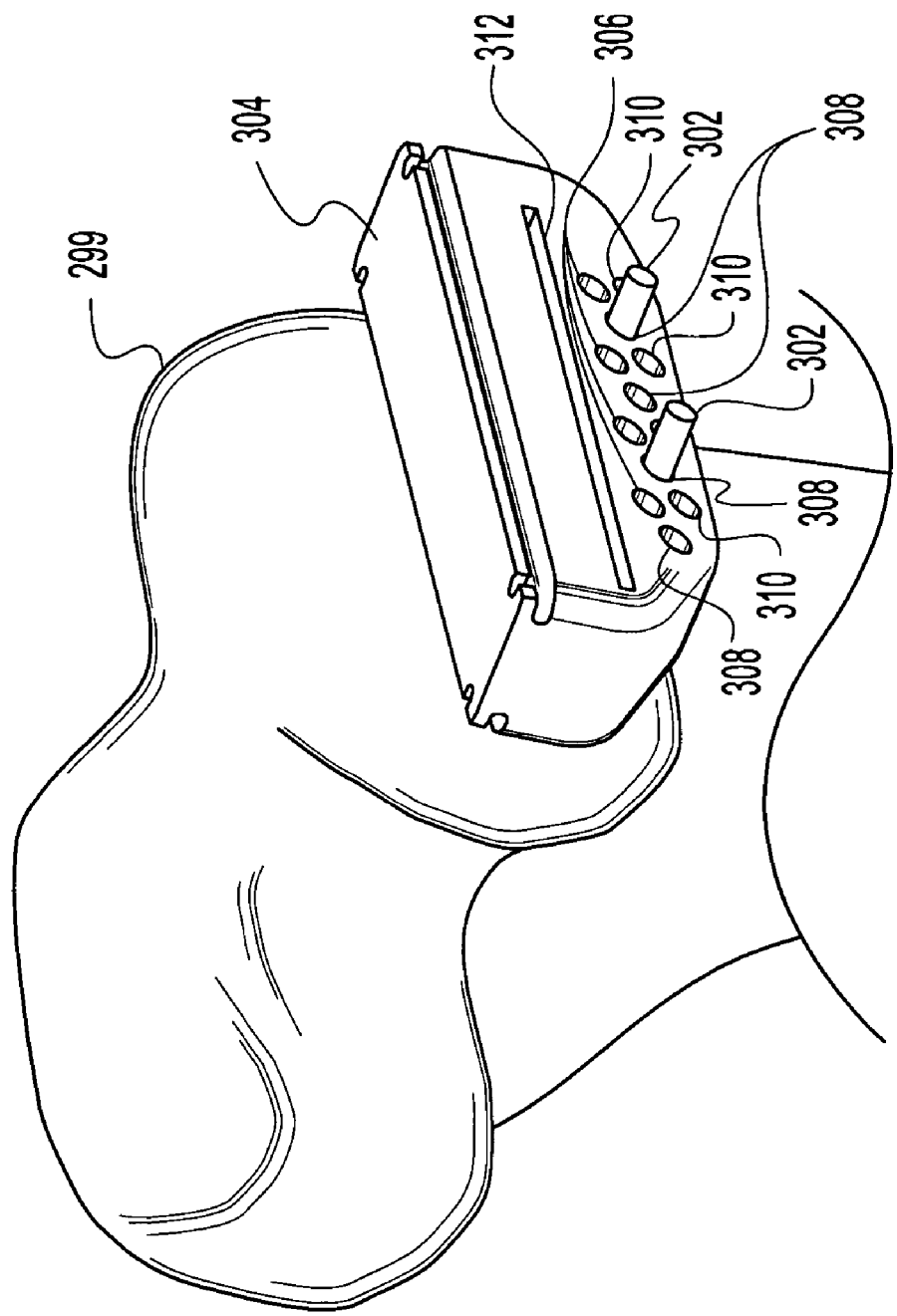
FIG. 7 is a perspective view showing a surgical component positioned using the datum of FIG. 6.
Figure 8:
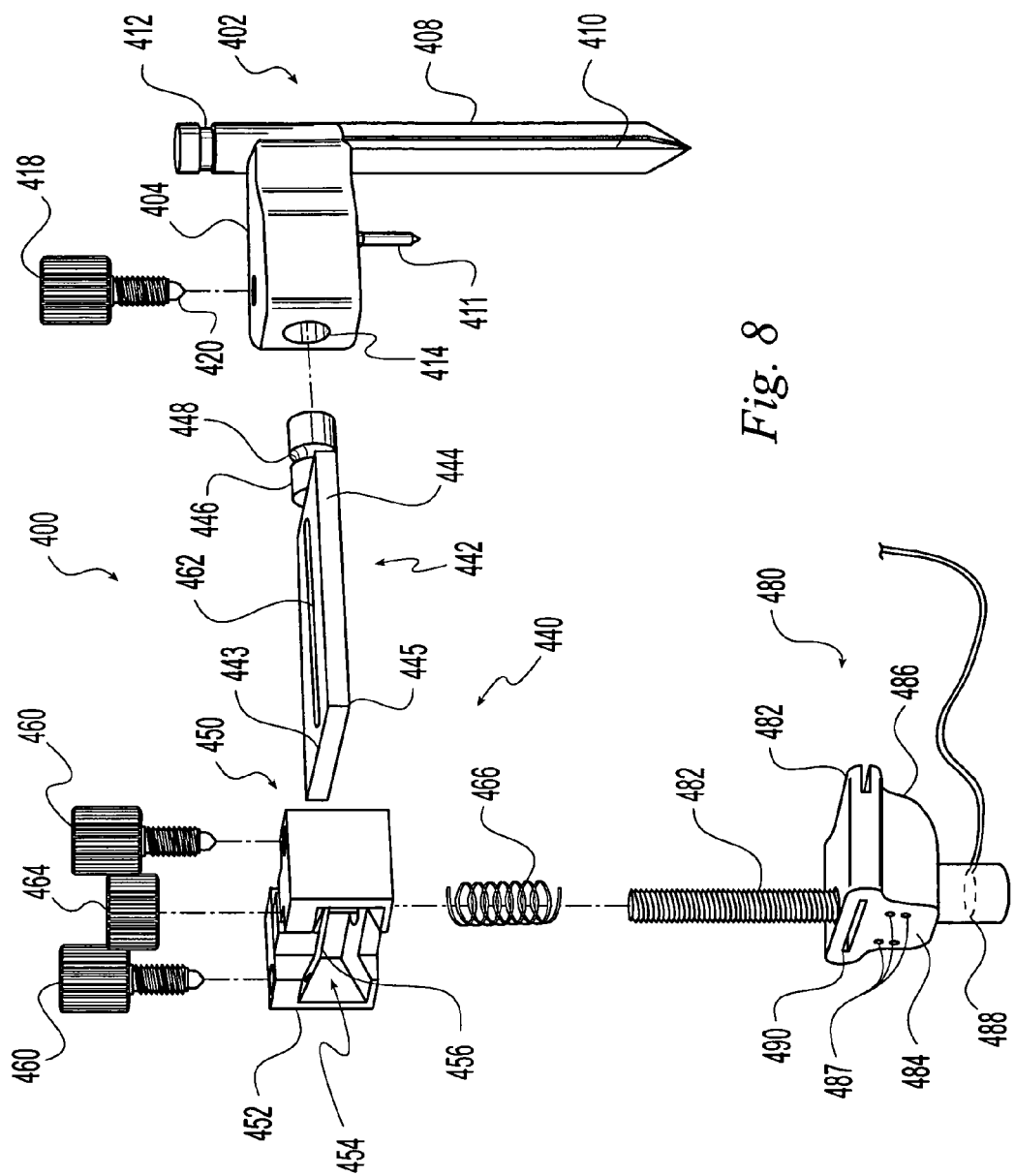
FIG. 8 is an exploded perspective view of an illustrative alternative arrangement for the navigated guide of FIG. 1 having an adjustment mechanism.

FIGS. 5-7 depict an illustrative alternative arrangement of the navigated orthopaedic guide of FIG. 1. further including an adjustment mechanism. The guide 200 includes a base member 202, a guide member 280 for establishing a datum, and a connecting link 240 connecting the base member 202 to the guide member 280. The base member 202 secures the guide 200 within the surgical navigation coordinate system. For example, the base member 202 may be secured to a bone adjacent the surgical site. The narrow elongated shape of the illustrative base member 202 permits it to fit into a narrow incision such as is used in a minimally invasive surgical technique. The illustrative base member 202 includes fixation holes 204 for receiving fixation members to secure the base member 202 to a bone. The fixation holes 204 may be angled to one side, as shown, to permit the fixation members to be inserted at an angle through a small incision and/or through a medially or laterally offset incision. The connecting link 240 permits adjustment of the guide member 280 relative to the base member 202 to permit the guide member 280 to be secured in a desired orientation relative to the bone. This adjustability is provided by adjustment mechanisms connecting the connecting link 240 to the base member 202 and the guide member 280.

The connecting link is connected to the base member 202 through a riser block 206 extending from the base member 202. A connecting link bolt 208 extends through a saddle washer 210, through the riser block 206, and into threaded engagement with a first locking knob 212. The connecting link bolt 208 includes a head 214 having a transverse bore 216. The connecting link 240 includes a cylindrical shaft 242 received by the transverse bore 216 for translation along and rotation about the bore 216 axis 217. As the first locking knob 212 is tightened onto the threads 218 of the connecting link bolt 208, the connecting link bolt 208 is drawn through the saddle washer 210 and riser block 206. The cylindrical shaft 242 of the connecting link 240 is drawn into abutment with a notch 220 in the saddle washer 210. tightening of the first locking knob causes the saddle washer 210 to lock the connecting link 240 relative to the base member 202 and prevent translation and rotation of the connecting link relative to the base member 202. The connecting link bolt head 214 may be radially enlarged, for example to form a shoulder 222, so that the connecting link bolt 208 will not inadvertently pass through the saddle washer 210 and riser block 206 if the cylindrical shaft 242 is disengaged from the transverse bore 216. The connecting link bolt 208 may include a non-circular shaft portion 224 corresponding to non-circular bores 226, 228 in the saddle washer 210 and riser block 206 to prevent the connecting link bolt 208 from rotating relative to the base member 202. By constraining the connecting link bolt 208 against rotation, the only relative motion between the connecting link 240 and the base member 202 is translation along and rotation about the transverse bore axis 217. Furthermore, constraining the connecting link bolt 208 facilitates tightening the first locking knob 212.

The riser block 206 may include a slit 230 dividing the riser block into two cantilevered spaced apart portions 232, 234. These portions 232, 234 act as springs to provide a broader range of tension adjustment in the adjustment mechanism than would be possible without a spring. With the slit 230, the first locking knob 212 may be easily adjusted to a tension sufficient to hold the cylindrical shaft 242 in a desired position within the transverse bore 216 when acted on by the weight of the guide member 280 yet still allow a user to move the cylindrical shaft 242 in the transverse bore 216 with hand pressure. The first locking knob 212 may then be tightened to lock the cylindrical shaft 242 in the final desired position.

The connecting link 240 is connected to the guide member 280 through a tab 244 extending from the connecting link 240. The tab 244 includes a bore 246 having a bore axis 248 angled relative to the transverse bore axis 217. The angle between these bore axes 217, 248 permits a second degree of rotational adjustment of the guide member 280 relative to the base member 202. The guide member 280 includes a yoke 282 having first and second spaced apart arms 284, 286. Each arm 284, 286 includes an elongated slot 288 that permits a second degree of translation adjustment of the guide member 280 relative to the base member 202. The tab 244 is received between the arms 284, 286 in sliding and pivoting relationship. A guide member bolt 290 extends through one of the arms 284, through the bore 246 in the tab 244, through the other arm 286, and into threaded engagement with a second locking knob 292. This arrangement constrains the guide member 280 to rotation about the tab bore axis 248 and translation along the elongated slot 288. The guide member bolt 290 includes a radially enlarged head 294 that abuts one of the yoke arms 284 to prevent the bolt from pulling through the slot 288. As the second locking knob 292 is tightened onto the threads 296 of the guide member bolt 290, the yoke arms 284, 286 are flexed together to grip the tab 244 of the connecting link 240. The spring action of the arms 284, 286 permits a range of tab 244 gripping tension such that the second locking knob 292 may be easily adjusted to a tension sufficient to hold the tab 244 in a desired position within the yoke 282 when acted on by the weight of the guide member 280 yet still allow a user to rotate the tab 244 within the yoke 282 with hand pressure. The second locking knob 292 may then be tightened to lock the tab 244, and consequently the guide member 280, in the final desired position. One or more optional lock washers 250 may be provided between the tab 244 and yoke 282. The washer may include teeth 252 to increase the grip between the yoke 282 and tab 244. Furthermore, the guide member bolt head 294 may include a non-circular profile received in a corresponding recess (not shown) adjacent the slot 288 to prevent the bolt 290 from turning when the second locking knob 292 is tightened. For example, the bolt head 294 may have flat sides 295 that fit within a flat sided countersink (not shown) surrounding the slot 288.

The guide member 280 includes means for establishing a datum in the surgical navigation system coordinate system. In the illustrative orthopaedic guide of FIG. 5, the guide member 280 includes guide holes 298 for guiding pins to establish a datum. The guide member 280 includes a tracking element, such as an electromagnetic coil 300, to permit the surgical navigation system to track the position and orientation of the guide member 280.

In use, the base member 202 is secured within the surgical navigation coordinate system by mounting it to an object known to the system. For example, the base member 202 may be mounted on a femur 299 as shown in FIG. 6. The narrow elongated shape of the illustrative base member 202 permits it to fit into a small incision. For example, the base member 202 may be inserted through a narrow medial or lateral incision adjacent to a knee joint. Furthermore, the fixation holes 204 may be angled, as shown, to permit fixation members to be inserted through such a medial or lateral incision. The first and second locking knobs 212, 292 are loosened to permit the guide member 280 to be moved relative to the base member 202. With the base member 202 positioned on the femur 299 as depicted in FIG. 6, the first locking knob 212 locks the medial-lateral position and the flexion angle of the guide member 280. The second locking knob 292 locks the varus-valgus position and resection depth of the guide member 280. The mechanism is manipulated until the surgical navigation system indicates that the guide member 280 is located in a desired position. The first and second locking knobs 212, 292 are then tightened to lock the guide member 280 in place relative to the base member 202. The guide member 280 may then be used to establish a datum for guiding a subsequent surgical component. For example, pins 302 may be inserted through guide holes 298 and into the femur 299. The navigated orthopaedic guide 200 may then be removed.

FIG. 7 illustrates a distal femoral cut block 304 mounted on the pins 302. The distal femoral cut block 304 includes holes 306, 308, 310 to receive the pins 302 and a cutter guide 312 for guiding a cutter to form a surface on the bone. The holes 306, 308, 310 may be provided as a plurality of rows of holes. Each row may provide a different level of resection. For example, one row of holes 308 may correspond to a predetermined nominal resection level. Additional rows 306, 310 may provide for cutting more or less bone should surgeon preference or the condition of the bone require it. By providing more holes in each row than the number of pins 302 used, the distal femoral cut block 304 may be adjusted anteriorly and posteriorly by lifting it off of the pins 302 and repositioning it on adjacent holes in the same row. With the cut block 304 positioned at the desired resection level and anterior-posterior position, additional fixation members may be inserted through some of the holes 306, 308, 310 to hold the cut block 304 in position while a cutter is guided to cut the bone 299.

The adjustable navigated orthopaedic guide 200 of FIGS. 5-7 has been shown configured to position a datum on the distal portion of a femur 299 to position a distal femoral cut guide 304. However, this adjustable guide may also be used to establish datums for other surgical components including cut guides such as a femoral finishing guide and/or a tibial cut guide. Also, as with the navigated orthopaedic guides of FIGS. 1-3 and 4, the guide of FIGS. 5-7 may itself serve as a datum to directly guide a subsequent surgical component.

FIGS. 8-11 depict another illustrative alternative arrangement for the orthopaedic guide of FIG. 1 further including an adjustment mechanism. The guide 400 includes a base member 402, a guide member 480, and a connecting linkage 440 for adjustably connecting the base member 402 and the guide member 480. The base member 402 includes a receiver block 404 for receiving the connecting linkage 440 and an anchor portion 406 for securing the guide within the surgical navigation coordinate system. The illustrative anchor portion 406 includes a primary mounting post 408 that may be driven into a bone. The primary mounting post 408 may include fins 410 to resist rotation of the base member 402 relative to the bone. A supplemental mounting post 411 may also be included to resist rotation of the base member 402. The supplemental mounting post 411 may be spaced radially from the primary mounting post 408 to create a larger moment arm to resist rotation. The base member 402 may include means for gripping the base member 402 to remove it from the bone. The illustrative anchor portion 406 extends above the base member 402 and includes an annular groove 412 that may be engaged by a pin puller, slap hammer, and/or other suitable instrument to extract the base member 402.

The connecting linkage 440 permits adjustment of the guide member 480 relative to the base member 402 to permit the guide member 480 to be secured in a desired orientation relative to the bone. This adjustability is provided by adjustment mechanisms connecting the connecting linkage 440 to the base member 402 and the guide member 480.

The connecting linkage 440 is connected to the base member 402 by way of a rotating support 442. In the illustrative example, the rotating support 442 includes a plate-like body 444 having a top surface 443, a bottom surface 445, and a trunnion 446 projecting from one end. The trunnion 446 is received in a bore 414 formed in the receiver block 404 for rotation about the bore 414 axis 416. A set screw 418 is threaded into the receiver block 404 to lock the rotating support 442 in place. The trunnion 446 may include an annular groove 448 to receive the tip 420 of the set screw 418. With the set screw 418 loosely engaging the groove 448, the rotating support 442 may rotate about the bore axis 416 but it is prevented from translating along the bore axis 416. tightening the set screw 418 locks the rotating support 442 in its rotated position.

An adjustment screw housing 450 is supported at an opposite end of the rotating support 442. The housing 450 includes a body 452 with a transverse opening 454 defined by opposed fulcrums 456. The rotating support is 442 is received in the opening 454 with its top and bottom surfaces 443, 445 in close fitting relationship to the vertices 458 of the opposed fulcrums 456. The fulcrums 456 permit the housing 450 to rock relative to the rotating support 442. A pair of angle adjustment screws 460 is threaded into the adjustment screw housing 450 transverse to and in communication with the opening 454 such that the screws 460 may engage the top surface 433 of the rotating support 442. The screws 460 are positioned in the housing 450 so that they are on opposite sides of the fulcrum vertices 458. By loosening one of the angle adjustment screws 460 and tightening the other, the housing 450 will pivot on the fulcrum vertices 458 to allow adjustment of the angle of the housing 450 relative to the support 442.

The connecting linkage 440 is connected to the guide member 480 by means of a portion of the guide member 480 connecting to the housing 450. In the illustrative example, a threaded rod 482 projects from the guide member 480 and extends through the housing, through the vertices 458 of the opposed fulcrums 456, through an elongated slot 462 formed in the rotating support 442, and into threaded engagement with an adjustment nut 464. A spring 466 is interposed between the guide member 480 and housing 450 to bias them apart. Tightening the adjustment nut 464 draws the threaded rod 482 into the housing 450 and thereby moves the guide member 480 toward the housing 450 and compresses the spring 466. Loosening the adjustment nut 464 allows the guide member 480 to move away from the housing 450.

The guide member 480 includes means for establishing a datum in the surgical navigation system coordinate system. In the illustrative orthopaedic guide of FIG. 8, the guide member 480 includes a guide member body 483 having a front face 484 and a back face 486. Guide holes 487 for guiding pins to establish a datum extend from the front face 484 to the back face 486. The guide member 480 includes a tracking element in the form of an electromagnetic coil 488 to permit the surgical navigation system to track the position and orientation of the guide member 480.

The guide member 480 may optionally include a datum surface to directly guide a subsequent surgical component. The illustrative orthopaedic guide of FIGS. 8-11 includes a datum surface in the form of an elongated cutter guide slot 490 extending from the front face 484 to the back face 486 to directly guide a subsequent surgical component. If the optional direct guiding datum surface is provided, the holes 487 may receive fixation members to hold the guide member 480 in place while the guide member 480 directly guides a subsequent surgical component. Unlike femoral cut guides, which typically must be provided in a range of sizes, a single tibial cut guide is often able to be used to cut a wide variety of tibial sizes. Therefore, it may be advantageous to provide a single, direct guiding, orthopaedic guide configured for tibial use as shown. However, the orthopaedic guide of FIGS. 8-11 may also be used to establish datums for a separate surgical component such as a tibial cut guide, femoral cut guide, implant, and/or other surgical component. It may also advantageously be used to establish datums for existing tibial cut guides to provide the benefits of surgical navigation technology with existing non-navigated components.

Figure 9:
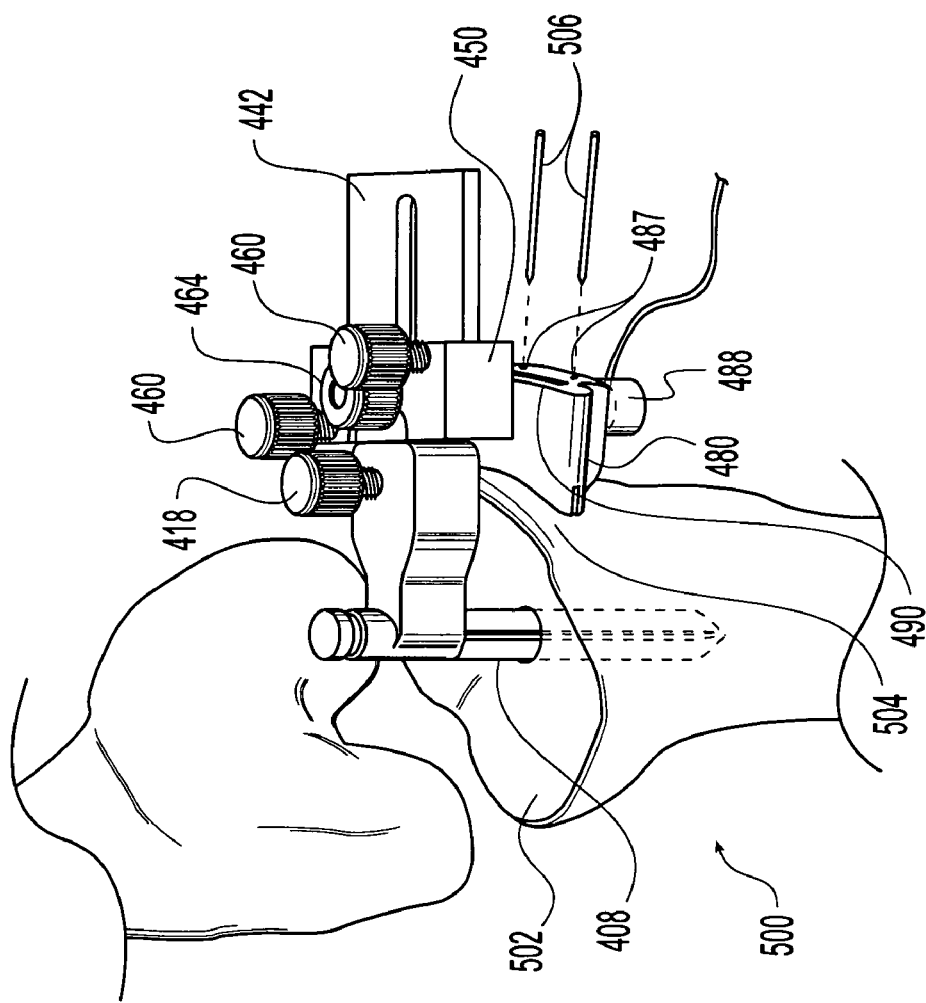
FIG. 9 is a perspective view of the navigated guide of FIG. 8 in use to establish a datum relative to a bone.
Figure 10:
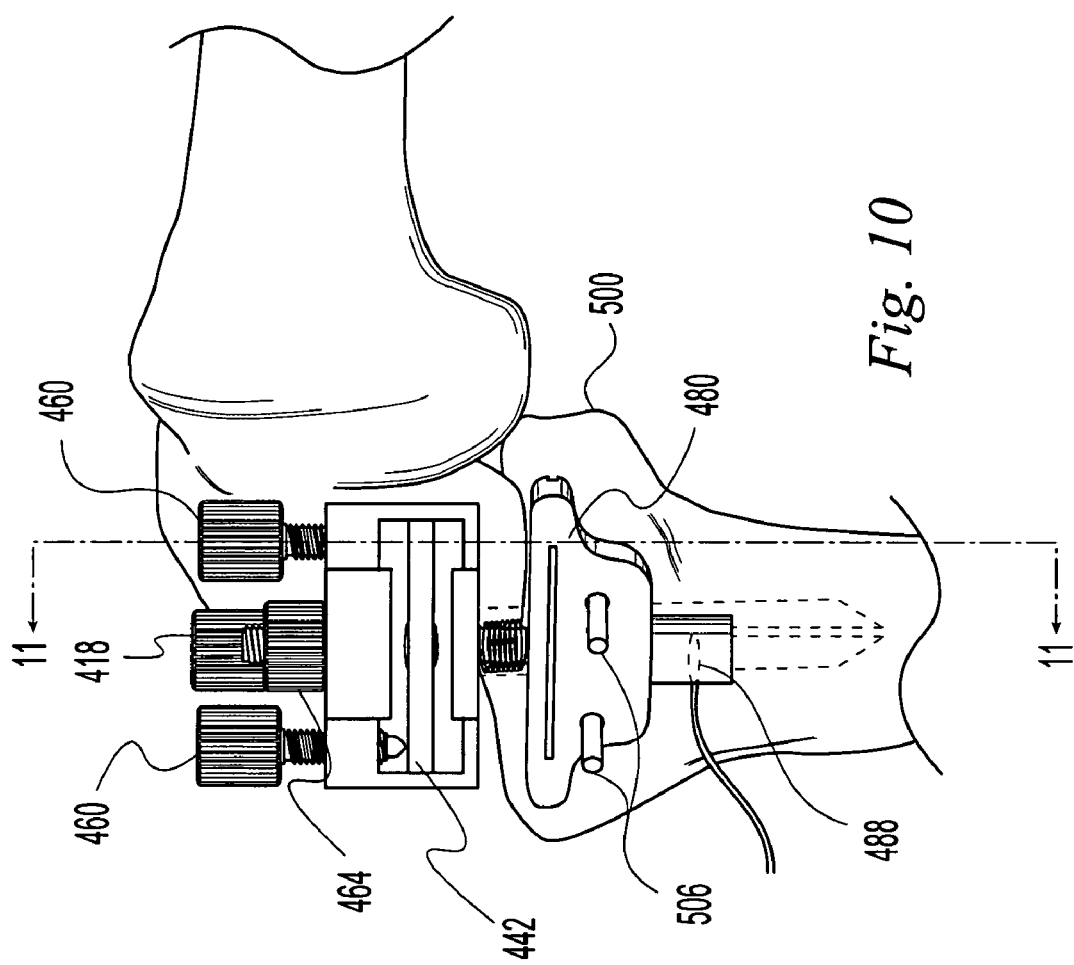
FIG. 10 is a perspective view of the navigated guide of FIG. 8 in use to establish a datum relative to a bone.
Figure 11:
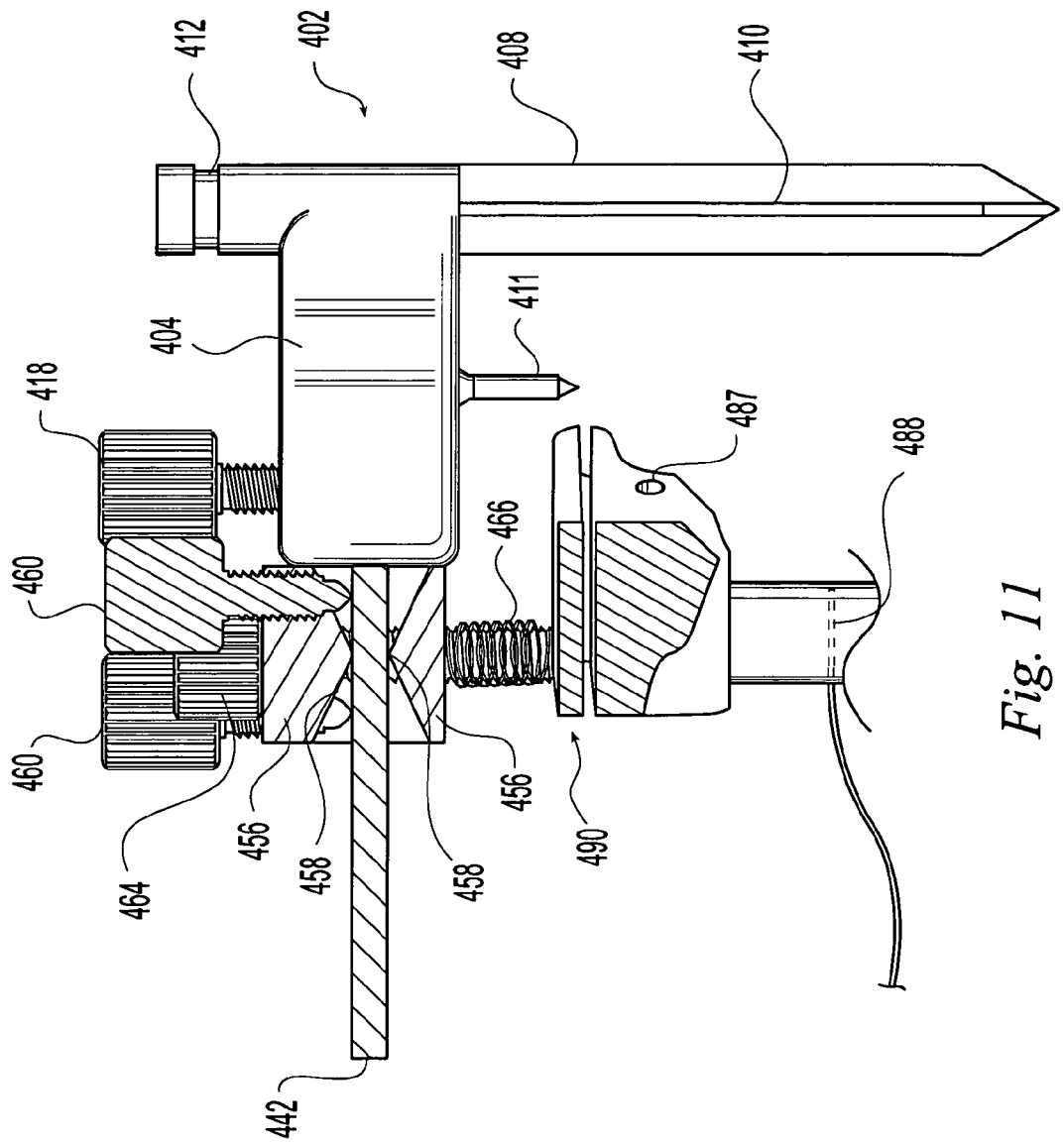
FIG. 11 is a cross sectional view taken along line 11-11 of FIG. 10 with the bone omitted for clarity.
Figure 12:
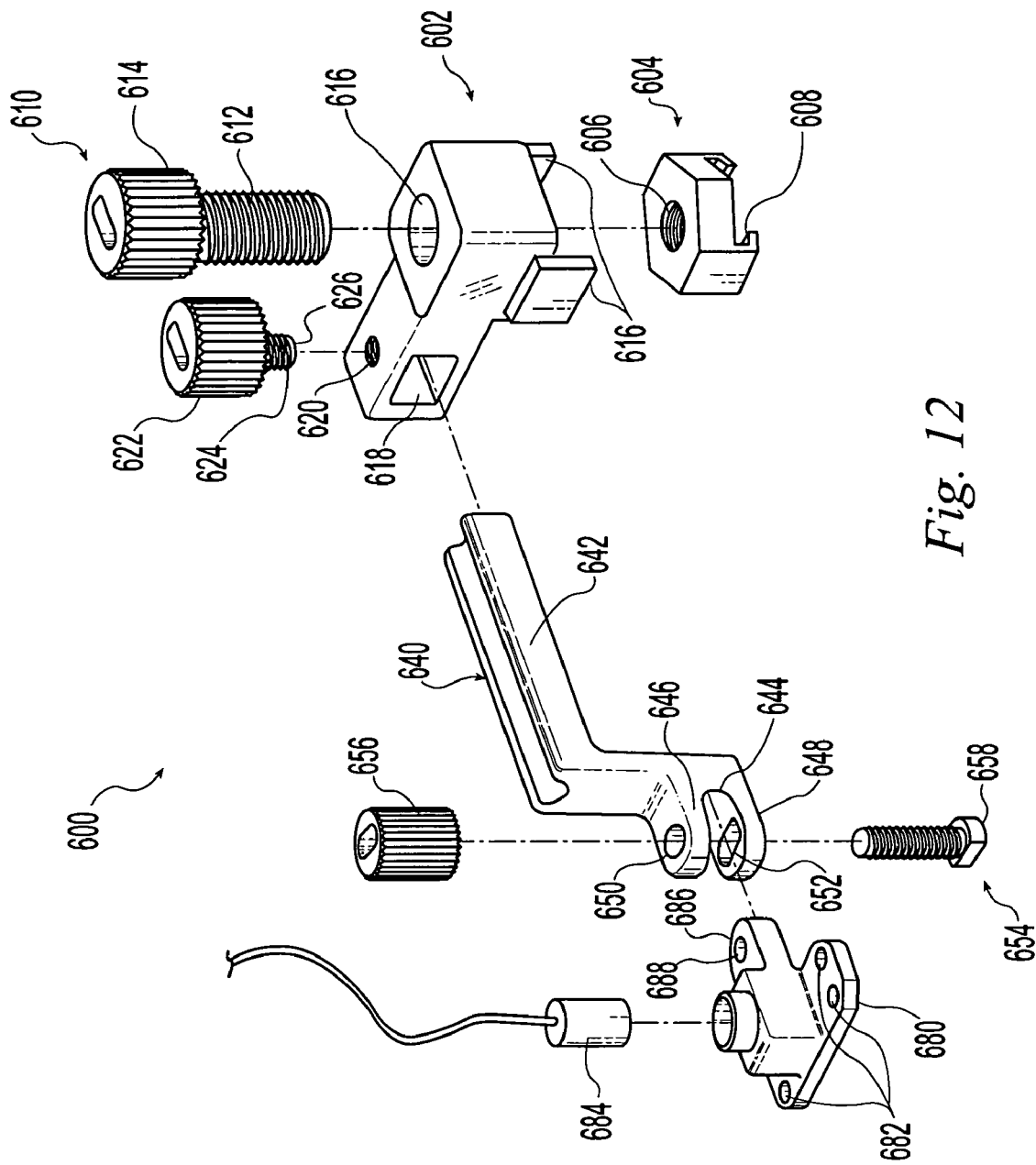
FIG. 12 is an exploded perspective view of an illustrative alternative arrangement for the navigated guide of FIG. 1 having an adjustment mechanism.
Figure 13:
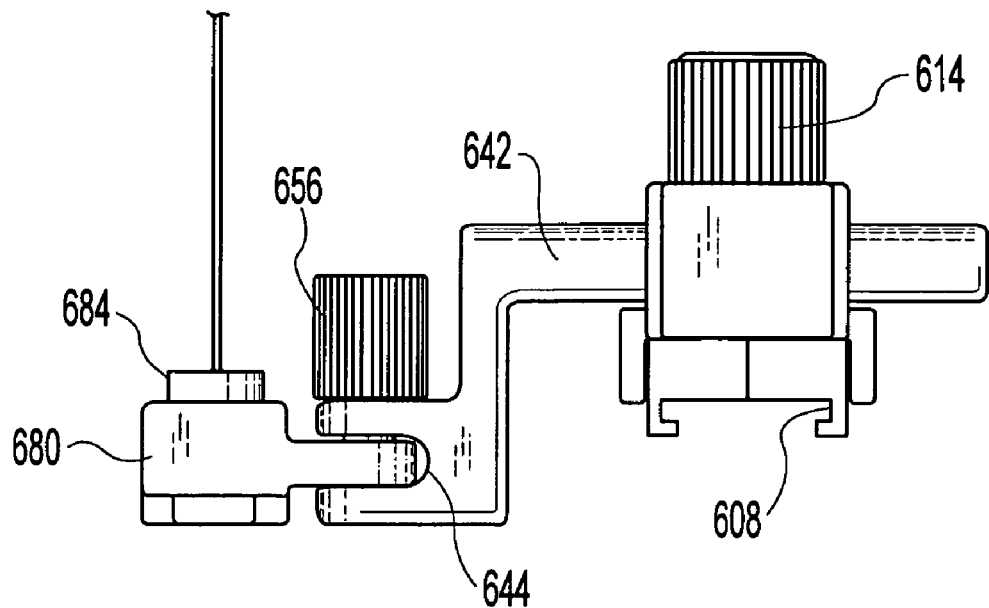
FIG. 13 is a front elevation view of the navigated guide of FIG. 12.
Figure 14:
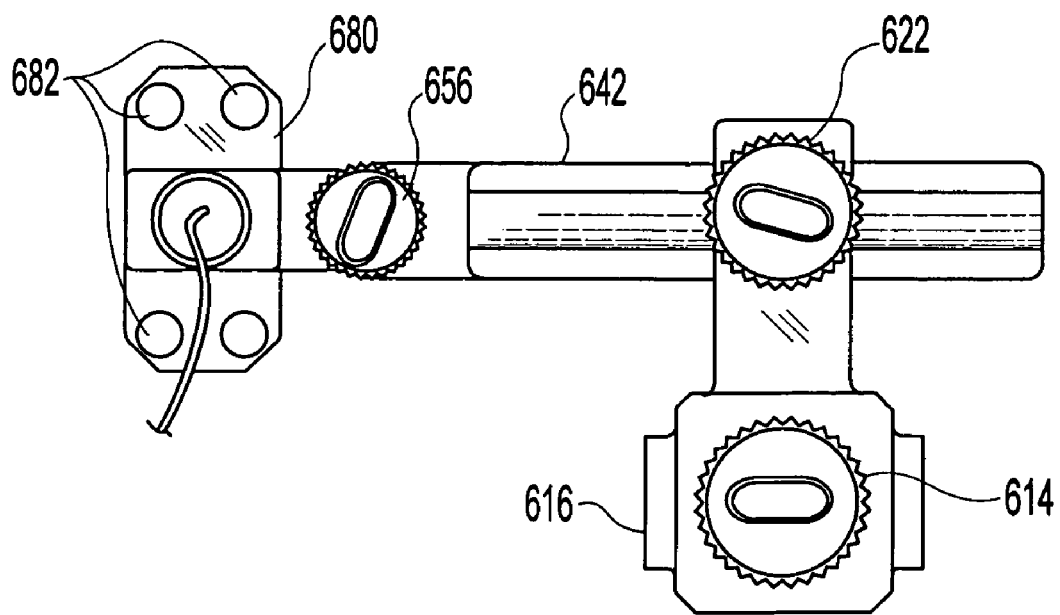
FIG. 14 is a top plan view of the navigated guide of FIG. 12.
Figure 15:
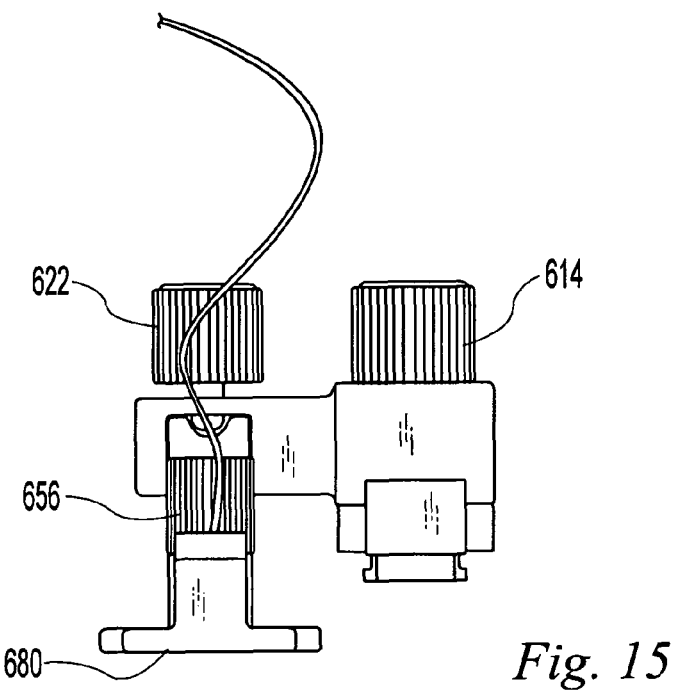
FIG. 15 is a side elevation view of the navigated guide of FIG. 12.

In use, the mounting post 408 is inserted into a bone to secure the guide 400 adjacent the bone, as shown in FIGS. 9 and 10. For use on a tibia 500, the mounting post 408 may be inserted through the proximal tibial surface 502 to position the guide member 480 adjacent the anterior tibial cortex 504. With both of the angle adjustment screws 460 loosened, the housing 450 and guide member 480 may be slid along the rotating support 442 to a desired position relative to the anterior tibial cortex 504. With the set screw 418 loosened, the rotating support 442, housing 450, and guide member 480 may be rotated to adjust the varus-valgus orientation of the guide member 480. By differentially tightening the angle adjustment screws 460, the housing 450 and guide member 480 may be angled about the fulcrum vertices 458 relative to the rotating support 442, as best seen in FIG. 11. This angle adjusts the posterior slope orientation of the guide member 480. Finally, by tightening or loosening the adjustment nut 464, the height of the guide member 480 may be varied to establish the resection depth position of the guide member 480. All of these adjustments may be made while the surgical navigation system is used to track the guide member 480. When the surgical navigation system indicates that the guide member 480 is in a desired position, the adjustment screws may be tightened to lock the position. The guide member 480 may now be used to establish a datum on the tibia 500, such as by inserting datum pins 506 through the holes 487 in the guide member 480 and into the anterior tibial cortex 504. The guide 400 may then be removed and the datum pins 506 may be engaged by a subsequent surgical component. For example, a cut block for guiding a cutter to resect the proximal tibial surface 502 may be engaged with the datum pins 506. Alternatively, the guide member 480 may directly establish a datum, such as with the guide slot 490, to guide a subsequent surgical component. For example, a cutter may be inserted in the guide slot 490 to guide the cutter to resect the proximal tibial surface 502.

The illustrative orthopaedic guide 400 of FIGS. 8-11 has been shown configured to directly guide a cutter to form a cut surface on the proximal tibia during a knee replacement surgical procedure. However, this orthopaedic guide 400 may also be used to directly guide or to establish datums for other surgical components and/or other surgical locations. For example, the orthopaedic guide 400 may be used to directly guide, or establish datums to guide, instruments or implants into a desired position relative to the tibia or femur of the knee joint, the femur or pelvis of a hip joint, and/or other components and locations.

Figure 16:
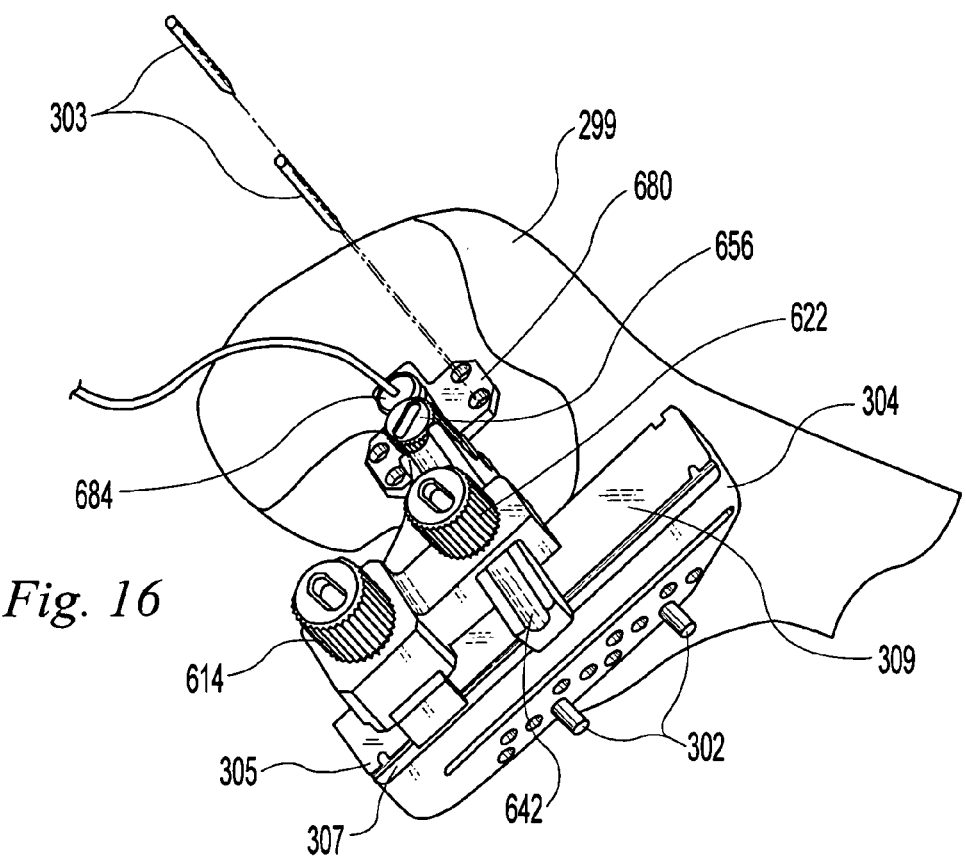
FIG. 16 is a perspective view of the navigated guide of FIG. 12 in use to establish a datum relative to a bone.

FIGS. 12-17 depict another illustrative alternative arrangement of the navigated orthopaedic guide of FIG. 1 further including an adjustment mechanism. The guide 600 includes a base member 602, a guide member 680 for establishing a datum, and a connecting link 640 connecting the base member 602 to the guide member 680. The base member 602 secures the guide 600 within the surgical navigation coordinate system. For example, the base member 602 may be secured to a bone adjacent the surgical site. Alternatively, the base member 602 may be secured to another surgical component as shown in FIG. 16 in which the illustrative base member 602 is secured to the distal femoral cut guide 304 of FIG. 7. The illustrative base member 602 includes a clamping nut 604 engageable with the distal femoral cut guide 304. The clamping nut 604 includes an axial threaded bore 606 and an undercut slot 608 transverse to the bore 606. A screw 610 includes a threaded shank 612 engageable with the axial bore 606 of the nut 604 and a knob 614. The shank 612 passes through a base clamp hole 616 in the base 602 and engages the nut 604. A pair of side wings 616 project downwardly from the base 604 to prevent the nut 602 from turning when the screw 610 is rotated. The clamping nut 604 permits clamping of the base 602 onto the distal femoral cut guide 304 in a selected relative position.

The connecting link 640 permits adjustment of the guide member 680 relative to the base member 602. This adjustability is provided by adjustment mechanisms connecting the connecting link 640 to the base member 602 and the guide member 680. The connecting link 640 includes an arm 642 at one end that slidingly engages an arm receiving opening 618 in the base 602 transverse to the undercut slot 608 such that the base 602 position can be adjusted relative to the distal femoral cut guide 304 in a first direction and the connecting link 640 can be adjusted relative to the base 602 in a second direction transverse to the first direction. In the illustrative example of FIGS. 12-17, the first and second directions are normal to one another. The base 602 includes a threaded hole 620 communicating with the arm receiving opening 618. A locking knob 622 includes a shank 624 that threads into the hole 620 such that the tip 626 of the shank 624 may be engaged with the arm 642 and tightened to lock the arm 642 relative to the base 602. The connecting link 640 includes a saddle 644 opposite the arm 642. The saddle 644 includes spaced apart sides 646, 648 which in turn include coaxially aligned bores 650, 652. The bores 650, 652 receive a clamping bolt 654 and a clamping knob 656 threads onto the bolt 654. One of the bores 652 may be non-cylindrical to receive a non-cylindrical head 658 of the bolt 654 to prevent the bolt 654 from turning when the knob 656 is turned.

The guide member 680 includes means for establishing a datum in the surgical navigation system coordinate system. In the illustrative orthopaedic guide of FIGS. 12-17, the guide member 680 includes guide holes 682 for guiding pins to establish a datum. The guide member 680 includes a tracking element, such as an electromagnetic coil 684, to permit the surgical navigation system to track the position and orientation of the guide member 680. The guide member 680 includes a tab 686 that engages the saddle 644. A through hole 688 in the tab 686 aligns with bores 650, 652 in the saddle such that the clamping bolt 654 may pass through one saddle bore 652, through the hole 688 in the tab 686, through the other saddle bore 650, and engage the clamping knob 656. The saddle 644 and tab 686 arrangement forms a hinge that permits the guide member 680 to be pivoted about the clamping bolt axis and locked in a desired angular position by tightening the clamping knob 656.

In use, the base member 602 is secured at the surgical site. For example, the base member 602 may be mounted on the bone. Alternatively, as shown in FIG. 16, the base member 602 may be mounted on the distal femoral cut guide 304. This provides a convenient mounting arrangement that facilitates the logical and rapid progression of the surgical procedure. The undercut slot 608 of the base clamping nut 604 engages a rail 305 and slot 307 formed along the top 309 of the distal femoral cut guide 304. The base 602 is slid along the distal femoral cut guide 304 to adjust the anterior/posterior position of the guide member 680 relative to the surgical site. The anterior/posterior position is locked by tightening the screw 610. The connecting link arm 642 is slid within the arm receiving opening 618 to adjust the medial/lateral position of the guide member 680 relative to the surgical site. The medial/lateral position is locked by tightening the knob 622. The guide member 680 is pivoted in the saddle 644 to adjust the interior/exterior rotation angle of the guide member 680 relative to the surgical site. The interior/exterior rotation angle is locked by tightening the knob 656. The mechanism is manipulated until the surgical navigation system indicates that the guide member 680 is located in a desired position. The locking knobs 614, 622, 656 are then tightened to secure the position. The guide member 680 may then be used to establish a datum for guiding a subsequent surgical component. For example, pins 303 may be inserted through guide holes 682 and into the femur 299. The navigated orthopaedic guide 600 and distal femoral cut guide 304 may then be removed.

Figure 17:
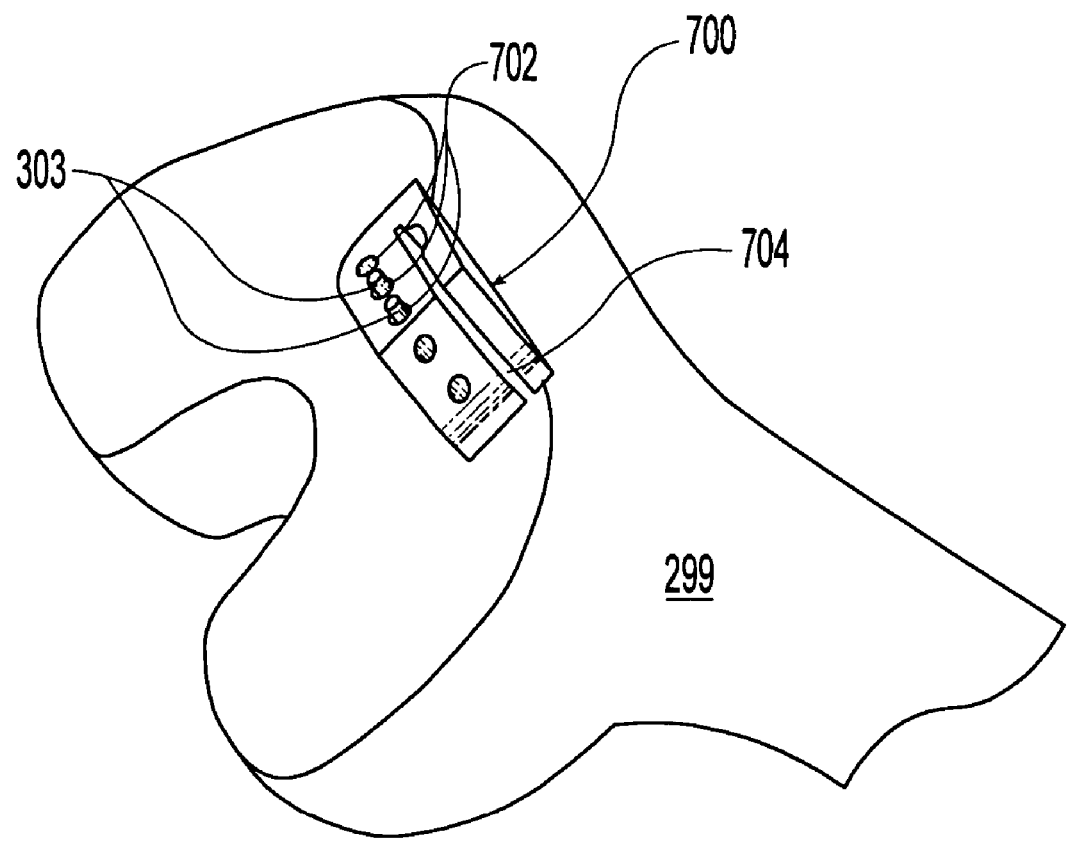
FIG. 17 is a perspective view showing a surgical component positioned using the datum of FIG. 16.
Figure 18:
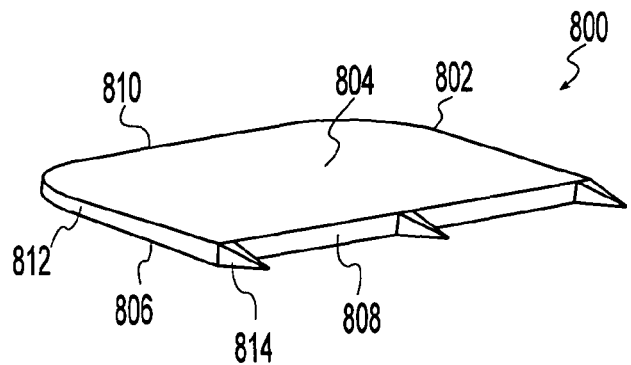
FIG. 18 is a perspective view of an illustrative alternative navigated guide.
Figure 19:
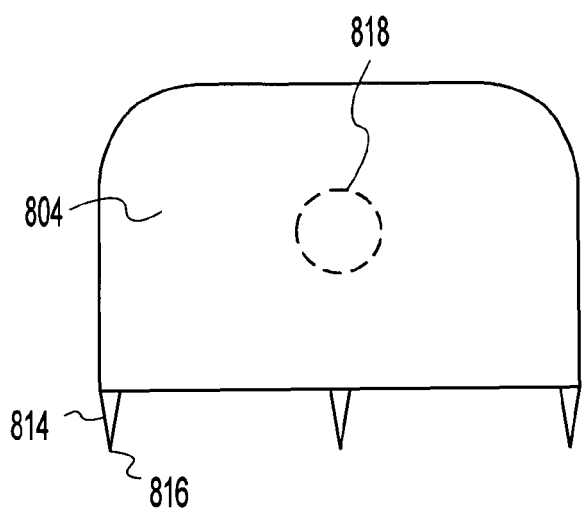
FIG. 19 is a top plan view of the illustrative navigated guide of FIG. 18.
Figure 20:
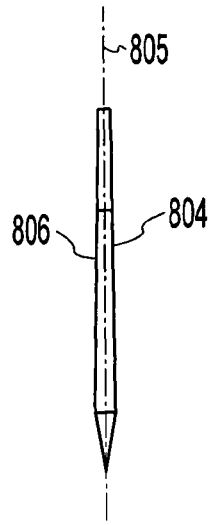
FIG. 20 is a side elevation view of the illustrative navigated guide of FIG. 18.
Figure 21:
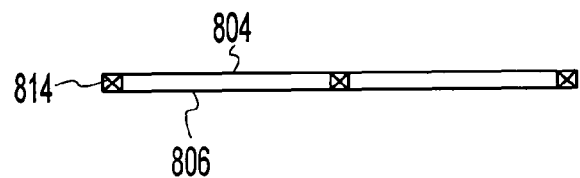
FIG. 21 is a front elevation view of the illustrative navigated guide of FIG. 18.

FIG. 17 illustrates an anterior rough cut guide block 700 mounted on the pins 303. The anterior rough cut guide block 700 includes holes 702 to receive the pins 303 and a cutter guide 704 for guiding a cutter to form a surface on the bone. With the anterior rough cut guide block 700 at the desired position as established by the pins 303, additional fixation members may be inserted through some of the holes 702 to secure the anterior rough cut guide block 700 while a cutter is guided to cut the bone 299. With the distal and anterior surfaces of the femur 299 cut, the proximal/distal, anterior/posterior, and internal/external rotation of a femoral implant are established. A finishing guide may be referenced to the distal and anterior cut surfaces of the femur 299 and placed in a desired medial/lateral position. The finishing cuts may then be made and the femoral implant inserted. The navigated orthopaedic guide of FIGS. 12-17 has been shown in use to position an anterior rough cut guide 700. However, it may also be used to position a posterior rough cut guide or other suitable surgical components.

Figure 22:
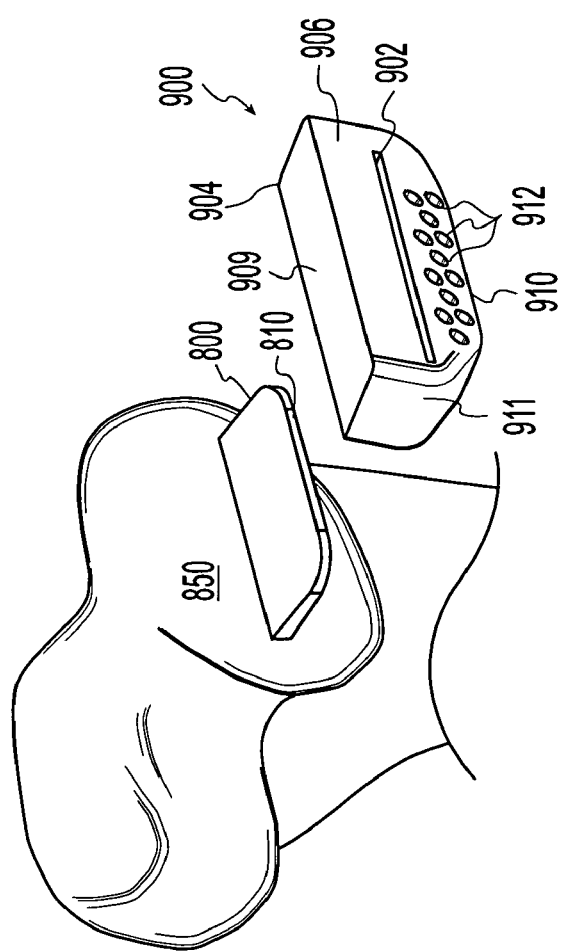
FIG. 22 is a perspective view of the navigated guide of FIG. 18 in use to establish a datum relative to a bone.

FIGS. 18-23 depict another illustrative embodiment of a navigated orthopaedic guide for establishing a datum to guide the placement of a surgical cut guide 900 (FIG. 22). The navigated guide 800 includes a body 802 having a top surface 804, a bottom surface 806, a leading edge 808, a trailing edge 810, and a peripheral sidewall 812. The top and bottom surfaces 804, 806 are relatively closely spaced such that the body 802 is in the form of a relatively thin plate shaped body. A centerplane 805 bisects the body 802 between the top and bottom surfaces 804, 806. The body 802 thickness is sized as a slip fit within a cut slot 902 in the cut guide 900. Thus, the body 802 is a solid representation of the cut plane established by the cut slot 902 and the body 802 serves as the datum to guide the cut guide 900. The centerplane 805 of the body corresponds to the center of the cut slot 902. The body 802 optionally tapers toward the centerplane 805 in the direction of the the trailing edge 810 to ease insertion of the trailing edge 810 into the cut slot 902. The guide 800 includes fasteners for attaching the body to a bone. In the illustrative embodiment, the fasteners are in the form of a plurality of spikes 814 formed integrally with the body 802 and projecting outwardly from the leading edge 808 parallel to the centerplane 805. Each spike 814 defines a rectangular pyramid tapering from the leading edge 808 to a sharp point 816 for penetrating bone. Alternatively, the fasteners may be cylindrical, conical, spiral, and/or any other suitable shape. The fasteners may be formed integrally with the body 802 as shown or they may optionally be provided separately from the body 802. If they are provided separately, the body may include suitable holes, grooves, channels, and/or other structures to permit the fasteners to hold the body 802 onto a bone.

The body 802 further includes a tracking element 818 to permit the surgical navigation system to track the position and orientation of the body 802. The tracking element 818 may be an electromagnetic coil, as shown. Alternatively, as with the other embodiments disclosed, the tracking element 818 may be in a form suitable for acoustic, visual, radio frequency, and/or other suitable surgical tracking system. The tracking element 818 may be embedded in the body 802 as shown. Alternatively, the tracking element 818 may be placed on the surface of the body 802 or placed on a support extending from the body 802. For example, the tracking element 818 may include an array of tracking elements in a tracking array removably mounted to the body 802 as is known in the art. Once the body 802 has been navigated to a desired position and secured, the array may optionally be removed. It is preferable to have a tracking element that does not extend beyond the surface of the body 802 or that is removable in order to improve visualization, ease insertion of the body into a cut slot, and/or otherwise streamline the body 802.

The illustrative cut guide 900 for use with the navigated guide includes a body 904 having a front surface 906, a back surface 908, a top surface 909, a bottom surface 910, and a peripheral sidewall 911. A slot 902 extends through the body 904 from the front surface 906 to the back surface 908. The slot 902 has a slot thickness from top to bottom, a slot width from side to side, and a slot depth from front to back defining a plane to guide a cutter (not shown) within a plane to form a planar surface on a bone. The cutter may include a saw blade, a rotary burr, a side cutting mill, and/or other suitable cutter. The slot 902 is a close slip fit over the body 802 of the navigated guide 800. The cut guide 900 further includes fixation holes 912 for receiving fasteners (not shown) to hold the cut guide 900 in position on a bone while the bone is cut. The fasteners may include pins, screws, and/or other suitable fasteners.

Figure 23:
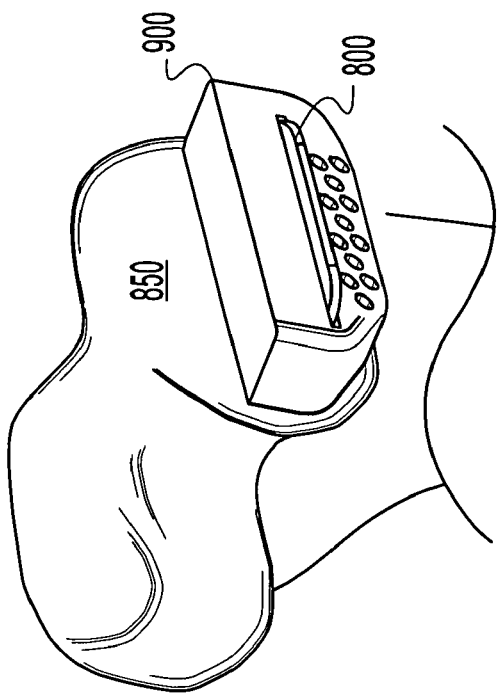
FIG. 23 is a perspective view showing a surgical component positioned using the datum of FIG. 22.

In use, the surgical navigation system is activated and used to manipulate the navigated guide 800 into a desired position relative to a bone (FIG. 22). For example, if it is desired to cut the distal femur 850 in knee replacement surgery, the guide 800 is navigated so that it lies in a plane corresponding to the desired plane of the distal femoral cut. The surgical navigation system may display the cut plane location relative to the bone for surgeon reference. The surgical navigation system may also provide visual, auditory, alpha numeric, and/or other position adjustment cues to the surgeon to indicate when the navigated guide 800 is in a desired position. The shape of the guide 800 further permits the surgeon to visually and tactilely verify the location of the cut plane. By visualizing the plate-like body 802 the surgeon can see where the cut plane intersects the surgical site. The rectangular plan form of the illustrative navigated guide 800 facilitates mentally extrapolating the cut plane through the surgical site. Similarly, the relatively broad, flat top and bottom surfaces 804, 806 and narrow leading and trailing edges 808, 810 facilitate the surgeon feeling the cut plane. By placing his fingers on the surfaces and edges, the surgeon can tactilely determine the cut guide position and orientation. When the cut plane is properly established, the navigated guide 800 is attached to the bone by driving the fasteners (FIG. 22). In the illustrative embodiment, the surgeon can strike the trailing edge 810 to force the spikes 814 into the bone. With the navigated guide 800 attached to the bone, the cut guide 900 is positioned by sliding the cut guide 900 slot over the body 802 and seating the cut guide 900 against the bone (FIG. 23). Fasteners may then be used to anchor the cut guide 900 relative to the bone. The navigated guide 800 is then pulled away from the bone through the slot 902 and the cut guide 900 is used to guide a cutter to cut the bone. The navigated guide 800 can be similarly used to establish a cut plane at any desired anatomic location for any surgical purpose.

Although examples of a navigated orthopaedic guide and its use have been described and illustrated in detail, it is to be understood that the same is intended by way of illustration and example only and is not to be taken by way of limitation. The invention has been illustrated with orthopaedic guides setting pins, guiding cutters, and establishing cut planes in specific locations related to knee replacement surgery. However, the orthopaedic guide may be configured to position other types of datums, for use with other types of surgical components, and at other locations within a patient's body. Accordingly, variations in and modifications to the orthopaedic guide and its use will be apparent to those of ordinary skill in the art, and the following claims are intended to cover all such modifications and equivalents.

What is claimed is:

1. A method of guiding a cutter at an orthopaedic surgical site to cut a bone, the method comprising:
   activating a surgical navigation system to track a position of a navigated guide by triangulating a signal transmitted by the navigated guide, the navigated guide comprising a plate shaped body representative of a cut plane;
   anchoring, by physical fastening, the navigated guide relative to the surgical site by a fastener in a desired position as indicated by the surgical navigation system;
   engaging a cut guide with the anchored navigated guide by sliding a cut slot in the cut guide over the plate shaped body of the navigated guide to align the cut slot with the cut plane;
   after said step of engaging, anchoring the cut guide to the surgical site; and
   after said step of anchoring the cut guide to the surgical site, removing the navigated guide through the cut slot.

2. The method of claim 1 further comprising viewing the navigated guide as a visual representation of the cut plane to verify correct cut plane positioning.

3. The method of claim 1 further comprising touching the navigated guide as a tactile representation of the cut plane to verify correct cut plane positioning.

4. The method of claim 1 further comprising:
   guiding a cutter with the cut slot to cut the bone in the cut plane.

5. The method of claim 1 wherein engaging a cut guide with the navigated guide comprises engaging a distal femoral cut guide with the navigated guide, the method further comprising:
   guiding a cutter with the distal femoral cut guide to cut a distal aspect of the femur.

6. The method of claim 1 wherein engaging a cut guide with the navigated guide comprises engaging a posterior femoral cut guide with the navigated guide, the method further comprising:
   guiding a cutter with the posterior femoral cut guide to cut a posterior aspect of the femur.

7. The method of claim 1 wherein engaging a cut guide with the navigated guide comprises engaging an anterior femoral cut guide with the navigated guide, the method further comprising:
   guiding a cutter with the anterior femoral cut guide to cut an anterior aspect of the femur.

8. A method of guiding a cutter at an orthopaedic surgical site to cut a bone, the method comprising:
   activating a surgical navigation system to track a position of a navigated guide by triangulating a signal transmitted by the navigated guide, the navigated guide comprising a plate shaped body representative of a cut plane;
   anchoring, by physical fastening, the navigated guide relative to the surgical site by a fastener in a desired position as indicated by the surgical navigation system;
   after said anchoring step, engaging a cut guide with the navigated guide by sliding a cut slot in the cut guide over the plate shaped body of the navigated guide to align the cut slot with the cut plane;
   after said step of engaging, anchoring the cut guide to the surgical site; and
   after said step of anchoring the cut guide to the surgical site, removing the navigated guide through the cut slot.

9. The method of claim 8 further comprising viewing the navigated guide as a visual representation of the cut plane to verify correct cut plane positioning.

10. The method of claim 8 further comprising touching the navigated guide as a tactile representation of the cut plane to verify correct cut plane positioning.

11. The method of claim 8 further comprising:
    guiding a cutter with the cut slot to cut the bone in the cut plane.

12. The method of claim 8 wherein engaging a cut guide with the navigated guide comprises engaging a distal femoral cut guide with the navigated guide, the method further comprising:
    guiding a cutter with the distal femoral cut guide to cut a distal aspect of the femur.

13. The method of claim 8 wherein engaging a cut guide with the navigated guide comprises engaging a posterior femoral cut guide with the navigated guide, the method further comprising:
    guiding a cutter with the posterior femoral cut guide to cut a posterior aspect of the femur.

14. The method of claim 8 wherein engaging a cut guide with the navigated guide comprises engaging an anterior femoral cut guide with the navigated guide, the method further comprising:
    guiding a cutter with the anterior femoral cut guide to cut an anterior aspect of the femur.

15. The method of claim 1 wherein the plate shaped body includes a tracking element which permits the surgical navigation system to track the position of the navigated guide.

16. The method of claim 15 wherein the tracking element is an electromagnetic coil.

17. The method of claim 8 wherein the plate shaped body includes a tracking element which permits the surgical navigation system to track the position of the navigated guide.

18. The method of claim 17 wherein the tracking element is an electromagnetic coil.

* * * * *